(12) United States Patent
Taniguchi et al.

(10) Patent No.: US 6,202,490 B1
(45) Date of Patent: Mar. 20, 2001

(54) NONDESTRUCTIVE TESTING APPARATUS

(75) Inventors: Ryosuke Taniguchi; Shinichi Hattori; Takahiro Sakamoto; Takashi Shimada, all of Tokyo; Kanji Matsuhashi, Hiroshima-ken, all of (JP)

(73) Assignees: Mitsubishi Denki Kabushiki Kaisha, Tokyo; Matsuhashi Techno Research Co., Ltd., Hiroshima-Ken, both of (JP)

( * ) Notice: Subject to any disclaimer, the term of this patent is extended or adjusted under 35 U.S.C. 154(b) by 0 days.

(21) Appl. No.: 09/562,037

(22) Filed: May 1, 2000

Related U.S. Application Data

(63) Continuation of application No. PCT/JP99/04719, filed on Aug. 31, 1999.

(30) Foreign Application Priority Data

Sep. 1, 1998 (JP) .................................................. 10-247520

(51) Int. Cl.⁷ .................................................. G01N 29/00
(52) U.S. Cl. .............................. 73/628; 73/630; 73/631; 73/579
(58) Field of Search ............................ 73/596, 579, 602, 73/627, 628, 629, 630, 631

(56) References Cited

U.S. PATENT DOCUMENTS

| | | | |
|---|---|---|---|
| 4,140,021 | * 2/1979 | Nomura et al. | 73/587 |
| 4,249,422 | * 2/1981 | Gaunaurd et al. | 73/589 |
| 4,446,733 | * 5/1984 | Okubo | 73/579 |
| 4,566,084 | * 1/1986 | Laine | 367/49 |

* cited by examiner

Primary Examiner—Richard A. Moller
(74) Attorney, Agent, or Firm—Sughrue, Mion, Zinn, Macpeak & Seas, PLLC

(57) ABSTRACT

A nondestructive testing apparatus is provided with a wave transmitter by a metal-based magnetostrictive vibrator, a magnetically excited current feeding device for feeding the magnetically excited current to the magnetostrictive vibrator, a wave receiver for detecting an acoustic elastic wave propagating through the measurement object, a filter for extracting a signal in a target frequency band to be measured, and an automatically amplifying rate controlling function-equipped amplifier for automatically controlling the amplifying rate so as to obtain a given magnitude amplitude regardless of the magnitude of the reflection wave or the transmission wave detected by the wave receiver, which constitute a feedback loop. The apparatus is further provided with a signal processor for processing the signal detected by the above-described wave receiver, and a display device for displaying the process result obtained by the signal waveform detected by the above-described wave receiver or the above-described signal processor.

5 Claims, 20 Drawing Sheets

NONDESTRUCTIVE TESTING APPARATUS

CROSS REFERENCE TO RELATED APPLICATION

This is a continuation of International Application PCT/JP99/04719, with an international filing date of Aug. 31, 1999.

TECHNICAL FIELD

This invention relates to a nondestructive testing apparatus for investigating, managing and evaluating construction and degradation of a structure or a material such as concrete in a building and an engineering work.

BACKGROUND ART

In order to enforce nondestructive testing of a concrete structure by using an elastic wave, it is necessary to precisely detect a reflection wave or a transmission wave propagating through the interior of the concrete. Namely, in view of a magnitude of a bridge, a road, dam, a building or the like to be inspected, a wave transmitter is required to have an ability to effectively injecting, into the measurement object, the elastic wave in the level of a frequency of vibration detectable even if the wave transmits the interior of the concrete for several tens cm to several tens m. Unlike a uniform material such as metal, in case of the concrete, if an acoustic wave in the band of about several MHz to be used for a metal material is introduced into the concrete, the attenuation is severe and the reach distance is short. Thus, it is impossible to use this acoustic wave for the concrete. For this reason, the band from several tens Hz to several tens kHz has to be utilized.

Conventionally, in the nondestructive testing of such a engineering building structure made of concrete, the measurement of the acoustic velocity or a thickness of the measurement object and an inference of an interior structure or a position of an abnormal portion are performed by a impact elastic wave method using an impact hammer, and by supersonic tests such as a pulse reflection method in which a probe using a piezoelectric vibrator is used as a wave transmitter for a supersonic wave, a transmission method and a resonance method.

The piezoelectric material constituting the piezoelectric vibrator that has been extensively used as a wave transmitter for a supersonic wave generates a strain in accordance with a magnitude of an electric field. The piezoelectric vibrator has a structure in which the piezoelectric material is sandwiched by electrodes and outputs a large vibration at a frequency at which its thickness corresponds to a half-wavelength of a longitudinal wave of the piezoelectric material. In general, a mechanical Q value of the piezoelectric material is high and the output efficiency of other than this mechanical resonance point is markedly degraded. Accordingly, in order to obtain a vibration in the band that is required for diagnosis of the concrete structure, the thickness of the piezoelectric vibrator should be several tens cm or more. However, it is very difficult to structure such a large size piezoelectric vibrator.

Namely, the probe using the piezoelectric vibrator is suitable for outputting a supersonic wave having a uniform frequency that is equal to or more than several tens MHz due to its characteristics. For this reason, there is a limit to the measurement in the nondestructive testing of the concrete structure in which the high frequency wave is remarkably attenuated. In particular, since it is difficult to obtain the energy of a low frequency wave that is needed for detecting the supersonic wave propagating through several tens m or longer by the piezoelectric vibrator, an impact hammer, a drop of a metal weight or the like is utilized.

The impact hammer is extensively used in a wide field for the reasons such as its simpleness and the magnitude of impact energy. The vibration band is several tens kHz. It is also applied to the nondestructive testing of a long and large concrete structure. In such a concrete structure, in order to obtain the reflection wave, a wave having a certain wavelength or more is required. However, the reflection wave might be buried in a signal of the impact. It is necessary to suitably adjust the intensity of the impact to meet the purpose of measurement. Namely, this largely depends upon the experiences or a sense of the tester. On the other hand, it is difficult to always keep the vibration force constant. The waveform observed varies for every impact. This leads to the fluctuation in evaluation. The vibration band is about 1 kHz but it is impossible to control the frequency as desired. In particular, it is difficult to detect the reflection wave in a short distance due to the affect of its reverberation wave.

The operation of a supersonic wave testing method using the piezoelectric vibrator will now be described.

A pulse reflection method and a transmission method are known as one of the measurement methods using the supersonic wave.

The pulse reflection method and transmission method are a method in which the pulsational supersonic wave is introduced from the surface of the structure, a time period until the reflection wave thereof comes back or a time period until the transmission wave propagates is measured, the acoustic propagation speed or the thickness or the distance to the reflection surface of the measurement object is obtained from the time period to thereby infer the interior structure or the absence/presence of the damage of the measurement object. On the other hand, the resonance method is a method in which a wavelength of the supersonic wave to be introduced into the measurement object is continuously changed by sweeping the frequency of a piezoelectric type oscillator to measure the resonance frequency and the plate thickness is measured from the frequency.

Furthermore, as a method of measuring an acoustic propagation speed or a thickness of the measurement object, there is a sing around method in which the introduced supersonic wave pulse is detected by a wave receiver at the end face and the detected pulse is used as a trigger to repeat the oscillation of the supersonic wave pulse. According to this method, a pulse row is generated at a constant cycle. This cycle is identical with the delay time for the pulse to propagate through the measurement object. It is therefore possible to obtain the acoustic propagation speed or the thickness of the measurement object.

The operation of the impact elastic wave method using the impact hammer will now be described.

The impact elastic wave method is a method in which the hammer impact is given to the measurement object so that a proper vibration owned by the object per se is stimulated and utilized in measurement. This method may be widely applied to a concrete, building stone, a brick material, a timber structure, a laminated material, an underground buried object or the like and is widely used as a nondestructive inspection method owing to its easiness to carry out the test.

FIG. 20 is a view showing the constitution of the impact elastic wave method using the hammer. In the drawing, reference numeral 311 denotes a hammer, reference numeral 312 denotes an impact receiving sensor, reference numeral 313 denotes an elastic wave receiver, reference numeral 314 denotes a storage oscilloscope and reference numeral 315 denotes a measurement object.

The operation of the reflection wave measurement method by hammering will now be described. The impact receiving sensor 312 is applied to the measurement objective surface of the measurement object 315 and the hammer 311 impacts the surface. In order to enhance the precision of measurement at this time, it is necessary to be attentive and adjust the intensity of the impact depending upon the measurement purpose or the material of the measurement object 315 and make sure that the impact is given only once. The elastic wave introduced into the measurement object 315 by the impact advances through the interior of the object 315 to be measured while reflected at an abnormal portion such as the confronting surface of the measurement objective surface, an internal structure or a damage or a gap, so that a part thereof reaches the impact receiving sensor 312. The output of the impact receiving sensor 312 passes through a filter and the waveform of the frequency corresponding to the purpose of measurement is extracted. When the pulse wave by the impact is given as a trigger signal of the storage oscilloscope 314 to catch the reflection wave, the time period from the hammer impact time to the arrival of the reflection wave can be measured. Thus, the distance up to the surface where the reflection wave is generated can be obtained from the measured time and the acoustic speed of the material.

In the conventional diagnosis of a concrete structure, since the acoustic elastic wave is generated by using the hammer or the wave sensor for the supersonic wave as described above, there are the following problems.

Supersonic Wave Test Method (1) The wave transmitter of the supersonic wave is suitable for outputting the acoustic elastic wave having a frequency of several tens kHz or more in view of the constitution of the vibrator of the piezoelectric type oscillator. For this reason, the method may be applied to the measurement for a material that is small in attenuation within a medium, such as metal, or a thin material. However, in case of a measurement object such as a concrete, where the attenuation within a medium is severe, the reached distance of transmission or reflection is short, and it is difficult to apply the method to the diagnosis of the long and large concrete structure.

(2) In order to identify the reflection wave, specialized knowledge is necessary. In particular, in case of a complicated shape or complicated internal structure, it is difficult to evaluate it.

(3) In the case where the propagation distance is long and the attenuation is severe or in the case where the reflection from the internal structure or the abnormal portion or the like of the measurement object is weak, the amplitude of the reflection wave to be detected would be minute in the same level as that of the noise. In such a case, the error would occur in detection of the reflection position or the speed.

(4) Any of the methods requires special signal processing or judgment from the shape of the reflection wave, demanding the special knowledge.

Impact Elastic Method (1) The hammer is bounded when the vibration is applied. As a result, the vibration application is performed plural times in a short cycle. For this reason, the reflection wave is hidden in the vibration signal or the signal cannot be discriminated from the reflection wave. Accordingly, an accurate measurement it is difficult. In order to avoid these, the tester has to be trained well for vibration application.

(2) Because the intesity of the vibration is adjusted manually, a signal suitable for the measurement, that is, the intensity enough to attain the reflection is not obtained, or the vibration is too high to become the intended impact signal, for outranging the dynamic range of the amplifier or the accelerator, and instead a complicated frequency component is generated. If the frequency component is near the proper vibration of the structure, an erroneous measured value is presented.

(3) Namely, there is no reproducibility in vibration and measurement result fluctuates according to the degree of skill of the tester.

(4) In the case where the thickness of the structure is relatively thin, a main component of the vibration by the hammer is sometimes lower than the proper frequency of the structure. In this case, the reflection wave is hidden by the reverberation after the vibration application, and it would be difficult to detect the reflection wave.

(5) It is impossible to perform the vibration control such as changing the vibration application frequency as desired or applying vibration under the feedback.

The present invention has been made to solve the above-described problems, and an object of this invention is to provide a nondestructive testing apparatus for a concrete structure with which a highly reproducible, stable, highly precise test can be performed without necessity for the skill or experience of an operator and which is easy and does not particularly require a special knowledge for evaluation.

DISCLOSURE OF THE INVENTION

A nondestructive testing apparatus in accordance with this invention is provided with a wave transmitter for injecting an acoustic elastic wave into a measurement object on the basis of a magnetically excited current, a magnetically excited current feeding device for feeding the magnetically excited current to the above-described wave transmitter, a wave receiver for detecting the acoustic elastic wave propagating through the measurement object and for outputting a received wave signal, a filter for putting a band limit to the above-described received wave signal, an automatically amplifying rate controlling function-equipped amplifier for amplifying the signal outputted from the above-described filter to a given amplitude and for outputting the signal to the above-described magnetically excited current feeding device, and a signal processor for extracting from the wave receiver a signal of an oscillation frequency of a positive feedback loop composed of the above-described wave transmitter, the above-described measurement object, the above-described wave receiver, the above-described filter, the above-described amplifier and the above-described magnetically excited current feeding device and for processing the signal.

Also, in the nondestructive testing apparatus in accordance with this invention, the above-described wave transmitter is a magnetostrictive vibrator composed of a magnetostrictive element, a magnetically exciting coil and a magnetic biasing magnet.

Also, the nondestructive testing apparatus in accordance with this invention is further provided with a display device for displaying the signal waveform detected by the above-described wave receiver or the process result obtained by the above-described signal processor.

Also, in the nondestructive testing apparatus in accordance with this invention, the above-described filter is a variable filter for selectively extracting a single frequency out of a plurality of resonance frequencies determined by the shape and the internal structure of the measurement object.

Furthermore, in the nondestructive testing apparatus in accordance with this invention, the above-described amplifier has a circuit for outputting the correction amount of the amplifying rate so that the above-described signal processor obtains the state information of the constitution of the measurement object in accordance with the correction amount.

BEST MODE FOR CARRYING OUT THE INVENTION

Embodiment 1

Figure 1:
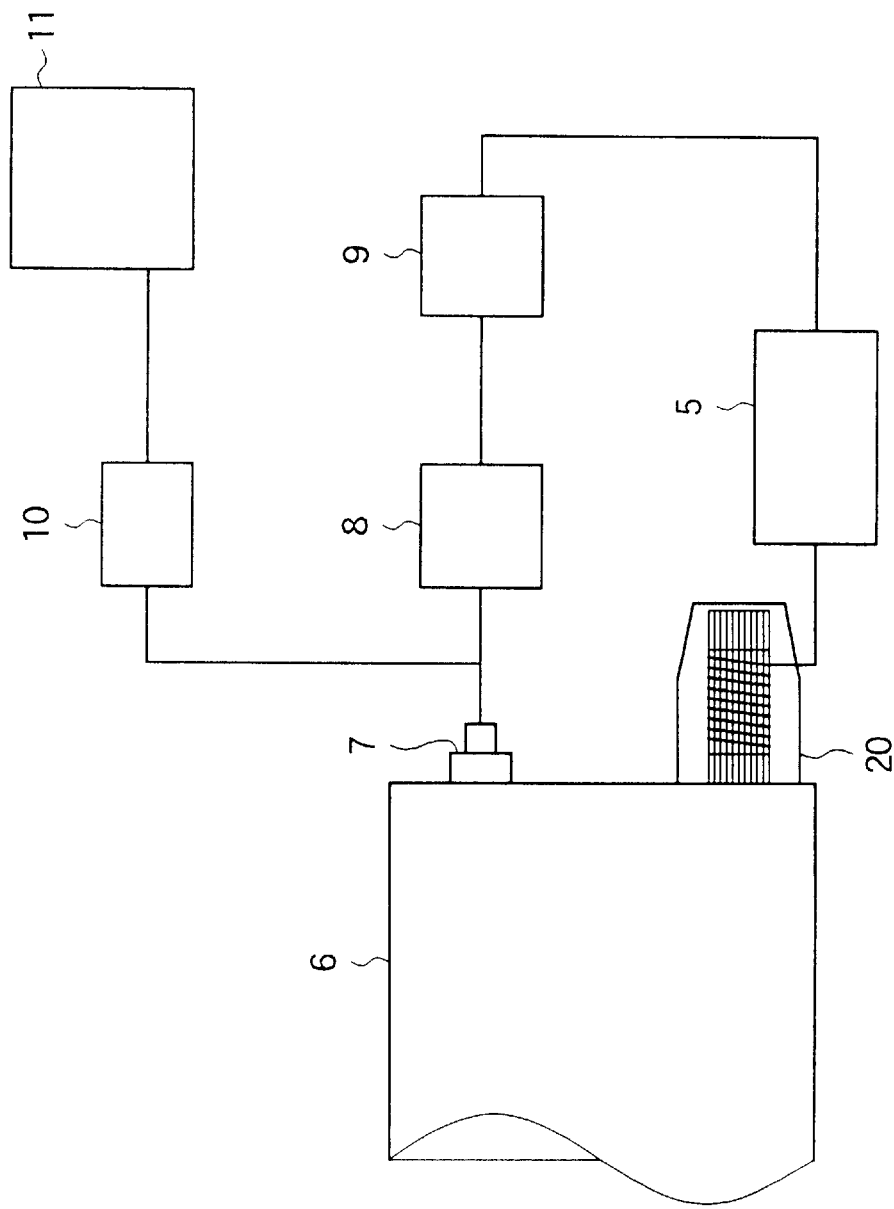
FIG. 1 is a view showing a system configuration of a nondestructive testing apparatus according to Embodiment 1 of this invention.
Figure 2:
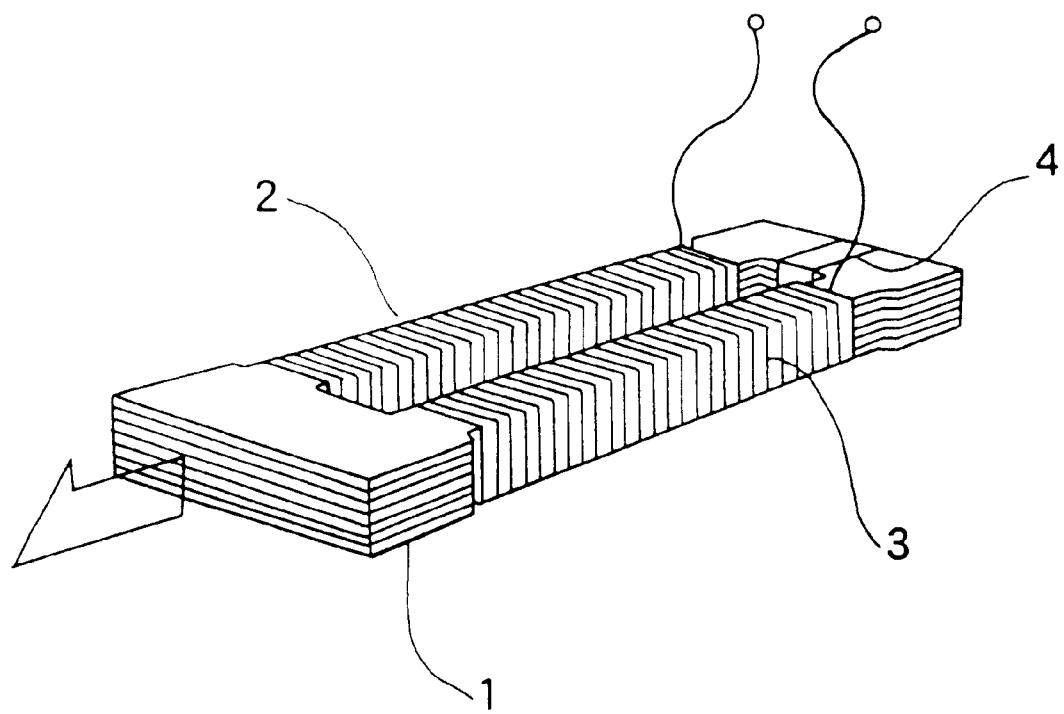
FIG. 2 is a view showing the constitution of a wave transmitter of the nondestructive testing apparatus according to Embodiment 1 of this invention.

A nondestructive testing apparatus according to Embodiment 1 of this invention will now be described with reference to the drawings. FIG. 1 is a view showing a system configuration of the nondestructive testing apparatus according to Embodiment 1 of this invention. FIG. 2 is a view showing the constitution of a magnetostrictive vibrator of the nondestructive testing apparatus according to Embodiment 1 of this invention. In the drawings, the same reference numerals denote the same or corresponding parts.

In FIG. 1, reference numeral 5 denotes a magnetically excited current feeding device, reference numeral 6 denotes an measurement object, reference numeral 7 denotes a wave receiver, reference numeral 8 denotes a filter, reference numeral 9 denotes an automatically amplifying rate controlling function-equipped amplifier, reference numeral 10 denotes a signal processor for processing a signal detected by the wave receiver 7, reference numeral 11 denotes a display device for displaying a signal waveform detected by the wave receiver 7 or a process result obtained by the signal processor 10, and reference numeral 20 denotes a wave transmitter.

In FIG. 2, reference numeral 1 denotes a magnetostrictive element, reference numeral 2 denotes a magnetostrictive vibrator, reference numeral 3 denotes a magnetically exciting coil, and reference numeral 4 denotes a magnetic biasing permanent magnet. Incidentally, this magnetostrictive vibrator 2 constitutes the wave transmitter 20. The arrow indicates a vibration direction.

The operation of the nondestructive testing apparatus according to Embodiment 1 will now be described.

A magnetostrictive material has such characteristics that when it is placed within the magnetic field, the material generates a slight strain in its direction and the magnitude of the strain and the direction of the strain are determined in accordance with the intensity and the direction of the magnetization. For the magnetostrictive element 1, thin plates made of a magnetostrictive material are cut out into a suitable shape, thermally and magnetically processed, and are subjected to the insulating process one by one. The layers are fixed to one another by an agglutinant. With such a laminate configuration, the eddy current loss generated by the magnetic excitation is reduced. The magnetostrictive vibrator 2 is formed by applying a solenoid type magnetically exciting coil 3 to a core material of the magnetostrictive element 1. When the magnetically excited current is caused to flow through this magnetically exciting coil 3, the magnetic field is generated in the interior of the magnetically exciting coil 3 in accordance with its magnitude. The magnetostrictive element 1 generates a strain in accordance with the magnitude of the generated magnetic field.

In the case where the magnetostrictive material having the characteristics that it changes in a constant direction regardless of the direction of the magnetization, the vibration of a cycle that is twice as large as that of the magnetic excited current, and it is impossible to obtain the oscillation as desired even if a feedback loop is formed. Accordingly, the magnetic biasing permanent magnet 4 is mounted on the magnetostrictive vibrator 2 to give a magnetic bias for suitably setting the operation point.

The resonant frequency point of the magnetostrictive vibrator 2 is determined by its length. For instance, a length of the minimum magnetostrictive element having a resonance frequency of 10 kHz is about 25 cm when the longitudinal wave speed of the magnetostrictive material as 5,000 m/sec. It is possible to readily produce the magnetostrictive vibrator having such a size. In comparison with the piezoelectric vibrator, the mechanical Q value of the magnetostrictive vibrator is low. Accordingly, the degradation in output efficiency is low even at a frequency other than the mechanical resonance point.

Also, since the magnetostrictive vibrator 2 has such a constitution, a stress caused by the vibration is not applied to the magnetically exciting coil 3. The direction of the laminate and the vibration direction are vertical, and a stress that peels the agglutinant between the layers is not applied. The magnetostrictive vibrator 2 thus has a mechanical strength equivalent to the material strength of the magnetostrictive material.

Incidentally, the magnetostrictive element 1 constituting the magnetostrictive vibrator 2 has a positive strain characteristic so that the length thereof is elongated with orientation when it is magnetically excited. The magnetostrictive element 1 is formed such that a plurality of magnetostrictive thin plates having a metal-based crystal constitution made of iron chromium alloy or iron cobalt alloy or the like are laminated one on another under the condition that the respective magnetostrictive thin plates are electrically insulated, and the plates are bonded integrally with a thermally curable resin to form an rigid body. A practical magnetostrictive thin plate having the positive strain characteristic may be suitably a Fe—Co magnetostrictive alloy disclosed in Japanese Patent Application Laid-Open No. Hei 10-88301 entitled "Method of manufacturing Fe—Co alloy plates" (for example, C: 0.008 wt %, Si: 0.08 wt %, Mn: 0.07 wt %, Co: 49.22 wt %, V: 1.546 wt %, Fe: the balance).

Since the lower the frequency of the magnetically excited current, the smaller the impedance of the magnetically exciting coil 3 will become, the lower the frequency of the applied voltage of the terminal of the magnetically excited coil 3 needed for feeding a given magnetically excited current, the lower the voltage will become. Accordingly, this is advantageous for the constitution of the magnetically excited current feeding device 5.

On the other hand, when the frequency of the magnetically excited current is increased, the loss within the laminate configuration is increased and the efficiency is degraded. The loss is increased in accordance with the thickness of the thin plates. In case of pure nickel well known as a magnetostrictive material, when the thin plate thickness is 0.2 mm, this leads to a reduction of the electric mechanical conversion efficiency by about 30% at 10 kHz. Accordingly, the magnetostrictive vibrator 2 is a wave transmitter suitable for applying the vibration that is equal to or less than ten and some kHz in view of its constitution.

In view of the above, the magnetostrictive vibrator 2 is more suitable than the impact hammer or the piezoelectric vibrator for the application of the vibration of not higher than several tens kHz that is needed for the nondestructive testing of the engineering work structure such as a concrete structure.

The magnetostrictive vibrator 2 is fixed onto the measurement objective surface of the measurement object 6 and an acoustic signal (vibration) of the measurement object 6 such as a concrete structure is detected by the wave receiver 7 such as an acoustic (vibratory) sensor to be converted into an electric signal. After a band limit is put to the electric signal converted by the filter 8, the amplifying rate is automatically controlled by the automatically amplifying rate controlling function-equipped amplifier 9 so that the signal has a given signal amplitude. This is inputted into the magnetically excited current feeding device 5 for feeding the magnetically excited current to the magnetostrictive vibrator 2 (wave transmitter 20) to form a positive feedback loop.

Figure 3:
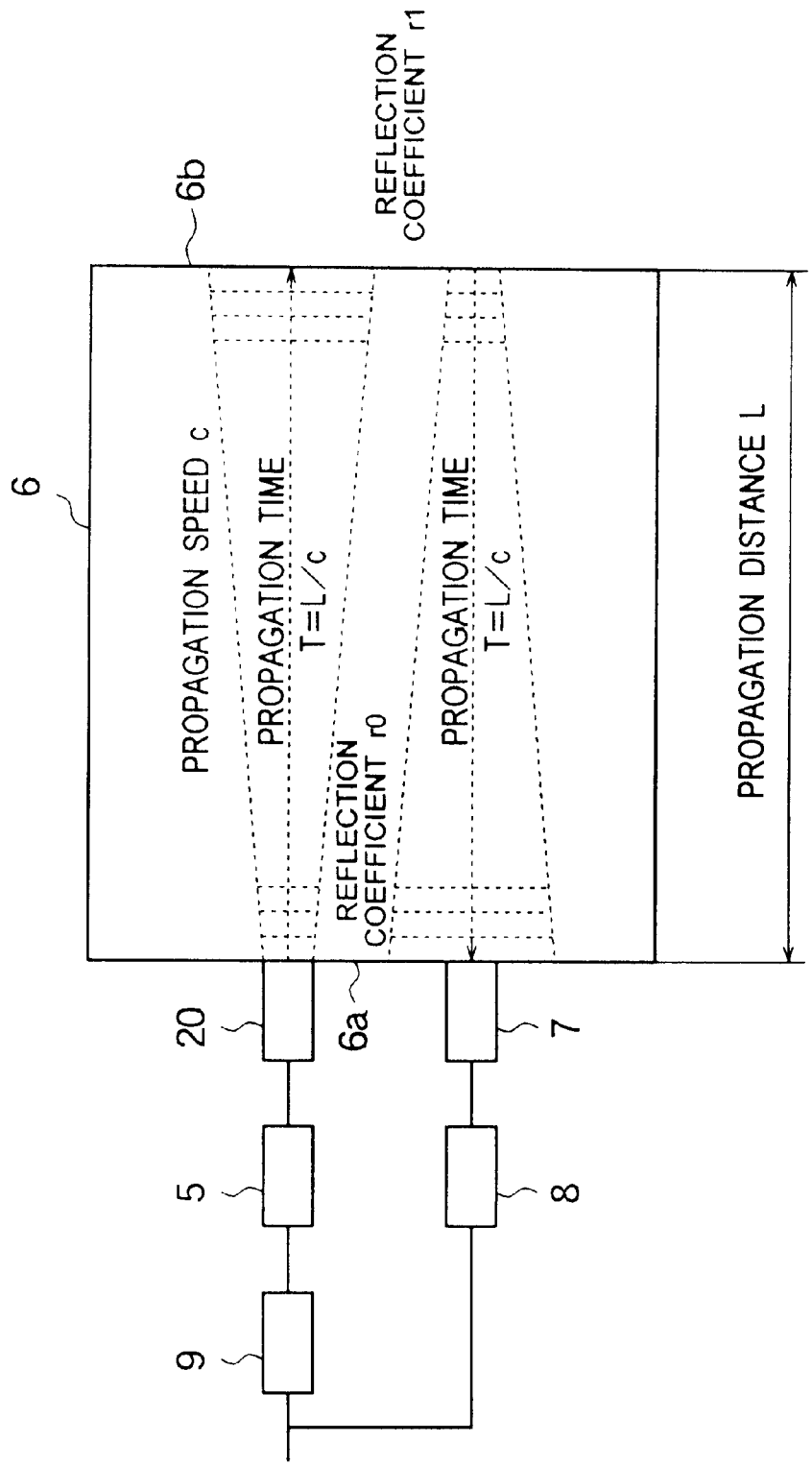
FIG. 3 is a view showing a positive feedback control system of the nondestructive testing apparatus according to Embodiment 1 of this invention.

FIG. 3 illustrates the constitution of a controlling system for feedback exciting and vibrating the reflection wave signal detected and for extracting only a frequency that meets the vibration condition under which the loop is constituted by the oscillation point, the reflection surface and the signal receiving end. In the drawing, (L) is the thickness (propagation distance) of the measurement object 6, (c) is the longitudinal acoustic elastic wave propagation speed within the measurement object 6 and (r1) is the reflection coefficient at the end face of the measurement object 6.

Having such a constitution, even if the reflection wave signal is small, the reflection wave that meets the vibration condition is automatically excited and vibrated by the feedback exciting and vibration so that the acceleration energy is applied to the frequency corresponding to the distance to the reflection surface. When the vibration condition is satisfied at the specific frequency, the application of the energy causes the frequency to grow, and the application is continued until the constant control at a constant signal/gain is finally performed.

Figure 4:
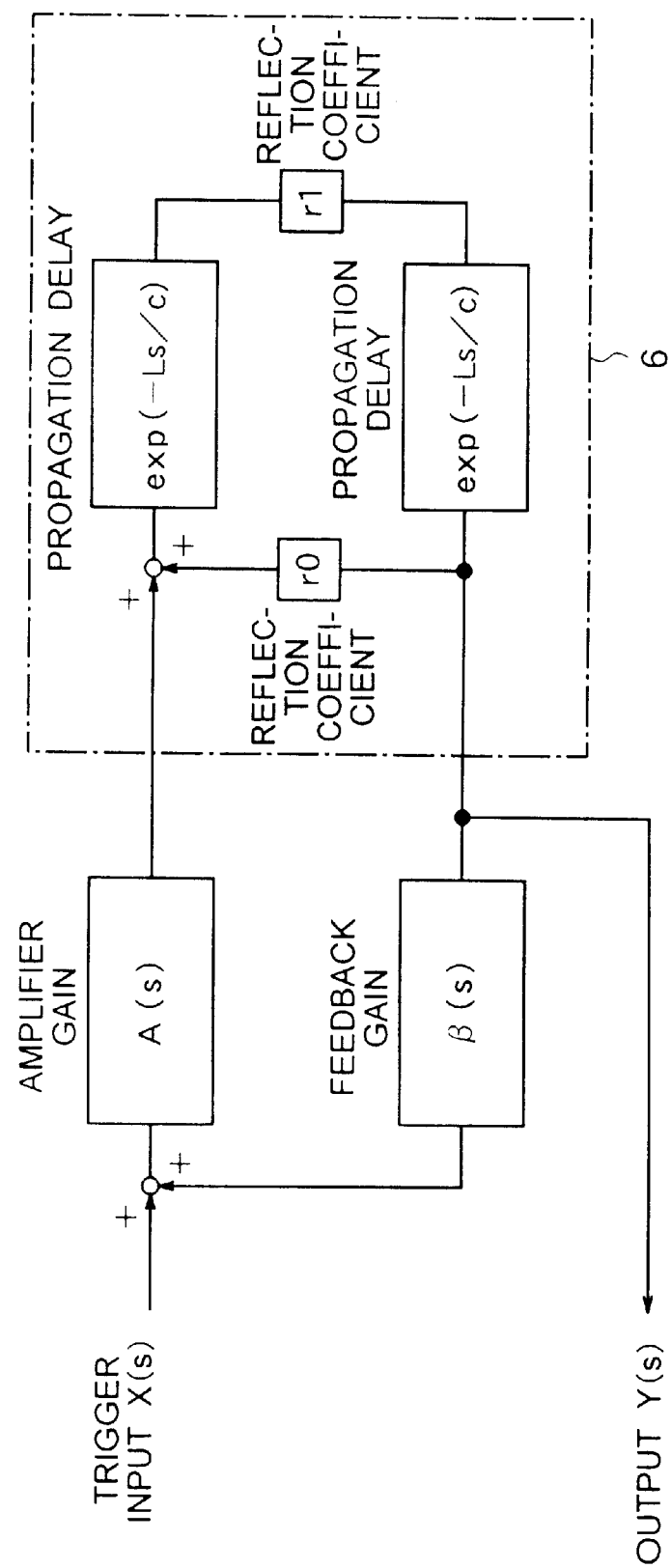
FIG. 4 is a block diagram showing a feedback control system of the nondestructive testing apparatus according to Embodiment 1 of this invention.

FIG. 4 is a block diagram of the above-described feedback controlling system. In the drawing, the propagation time T is obtained by the following formula where c is the propagation speed of the longitudinal elastic wave of the measurement object 6 and L is the distance to the end face (or the internal reflection surface):

$$T = L/c$$

The reflection occurs at the end face 6b and this reflection coefficient is given as r1. The reflection wave propagates toward an oscillation surface through the measurement object 6 and reaches an oscillation surface 6a in the propagation time T. This wave is further reflected at the oscillation surface 6a and the propagation to the end face 6b is repeated again. The reflection coefficient at the oscillation surface 6a is given as r0.

Now assume that X is the trigger input of the oscillation and Y is the output at the wave receiver 7. Also, assume that $\beta$ is the feedback gain of the positive feedback loop and A is the amplifier gain. Here, the amplifier gain A represents the total gain of the automatically amplifying rate controlling function-equipped amplifier 9, the magnetically excited current feeding device 5 and the wave transmitter 20, and the feedback gain $\beta$ is the total gain of the wave receiver 7 and the filter 8.

The automatically amplifying rate controlling function-equipped amplifier 9 is an amplifier with the PID control function composed of elements for calculating a root mean square (RMS) of the input signal, i.e., a proportional element (P), an integration element (I) and a differentiating element (D).

If the propagation delay to the reflection surface is represented by a Laplace transform, the formula is given as follows:

$$e^{-\frac{L}{c}s}$$

Furthermore, the propagation delay from the interface is given as follows:

$$e^{-\frac{L}{c}s}$$

Therefore, the output Y is given as the formula (1):

$$Y = \frac{A \cdot r_1 \cdot e^{-2\frac{L}{c}s}}{1 - (r_1 r_0 + r_1 A\beta) \cdot e^{-\frac{L}{c}s}} \cdot X \quad (1)$$

Incidentally, in the case where the positive feedback is not effected, the output is given as $A\beta=0$, and the output Y is as follows:

$$Y = \frac{r_1 \cdot e^{-2\frac{L}{c}s}}{1 - r_1 r_0 \cdot e^{-2\frac{L}{c}s}} \cdot X = r_1 \cdot e^{-2\frac{L}{c}s} \cdot \left(1 + r \cdot e^{-2\frac{L}{c}s} + r^2 \cdot e^{-4\frac{L}{c}s} + \Lambda\right)X \quad (1a)$$

where $r=\sqrt{(r_1 r_0)}$. The reflection coefficient is $r<1$ although depending upon the characteristics of the measurement object.

As is apparent from the expansion (1a), after the generation of the trigger signal (t=0), the first wave $r_1 X$ appears with $t=2L/c$ (longitudinal elastic wave) and thereafter the second and third reflection waves are detected, and attenuated as follows: $r_1 r X, r_1 r^2 X, r_1 r^3 X, \Lambda$ By the positive feedback, $r_1 r_0$, the denominator of the formula (1a) is $r_1 r_0 + r_1 A\beta$.

If $r_1 r_0 + r_1 A\beta = K$, the formula (1) outputs at the cycle $T=2L/c$ by the positive feedback, a cyclic waveform formula (2) in which the waveform in each cycle is $K^{2m} \cdot X(0 \text{ t } T)$.

$$Y = \quad (2)$$

$$A \cdot r_1 \cdot e^{-2\frac{L}{c}s} \cdot \left(1 + K^2 \cdot e^{-2\frac{L}{c}s} + K^4 \cdot e^{-4\frac{L}{c}s} + \Lambda + K^{2m} \cdot e^{-2\frac{L}{c}s} + \Lambda\right) \cdot X$$

$A\beta$ is adjusted to an appropriate value so that the output is constantly issued.

Subsequently, the oscillation condition is clarified. The oscillation condition is obtained from the formula (1) when the denominator is not smaller than 0, and is expressed by the following formula (3).

$$1 - (r_1 r_0 + r_1 A\beta) \cdot e^{-2\frac{L}{c}s} \le 0 \quad (3)$$

Namely, this may be replaced as follows:

$$e^{2\frac{L}{c}s} \le r_1 r_0 + rA\beta \quad (3a)$$

Namely, the oscillation condition may be represented as follows:

① The gain of $(r_1 r_0 + r_1 A\beta)$ is 1 or more than 1.
② The phase of $e^{-2L s/c}$ is equal to the phase of $(r_1 r_0 + r_1 A\beta)$.

Where $(r_1 r_0 + r_1 A\beta)$ is a real number, i.e., when there is no frequency dependency, $\omega = c/L \cdot n\pi$ according to the condition ii).

Namely, when $f=c/2L$. $n(n=1,2, \ldots )$, the oscillation condition is met. Namely, n=1 is a basic frequency, n=2 is a secondary harmonic, and onward $f_n=c/2L$. n is the n-th harmonic.

According to the gain condition i) and the phase condition ii), the oscillation condition is determined. A suitable frequency characteristic is given to the filter and the amplifier within the positive feedback to thereby control the oscillation by the harmonics. A low band pass filter (LPF) is applied as a filter for suppressing the harmonics.

Figure 5:
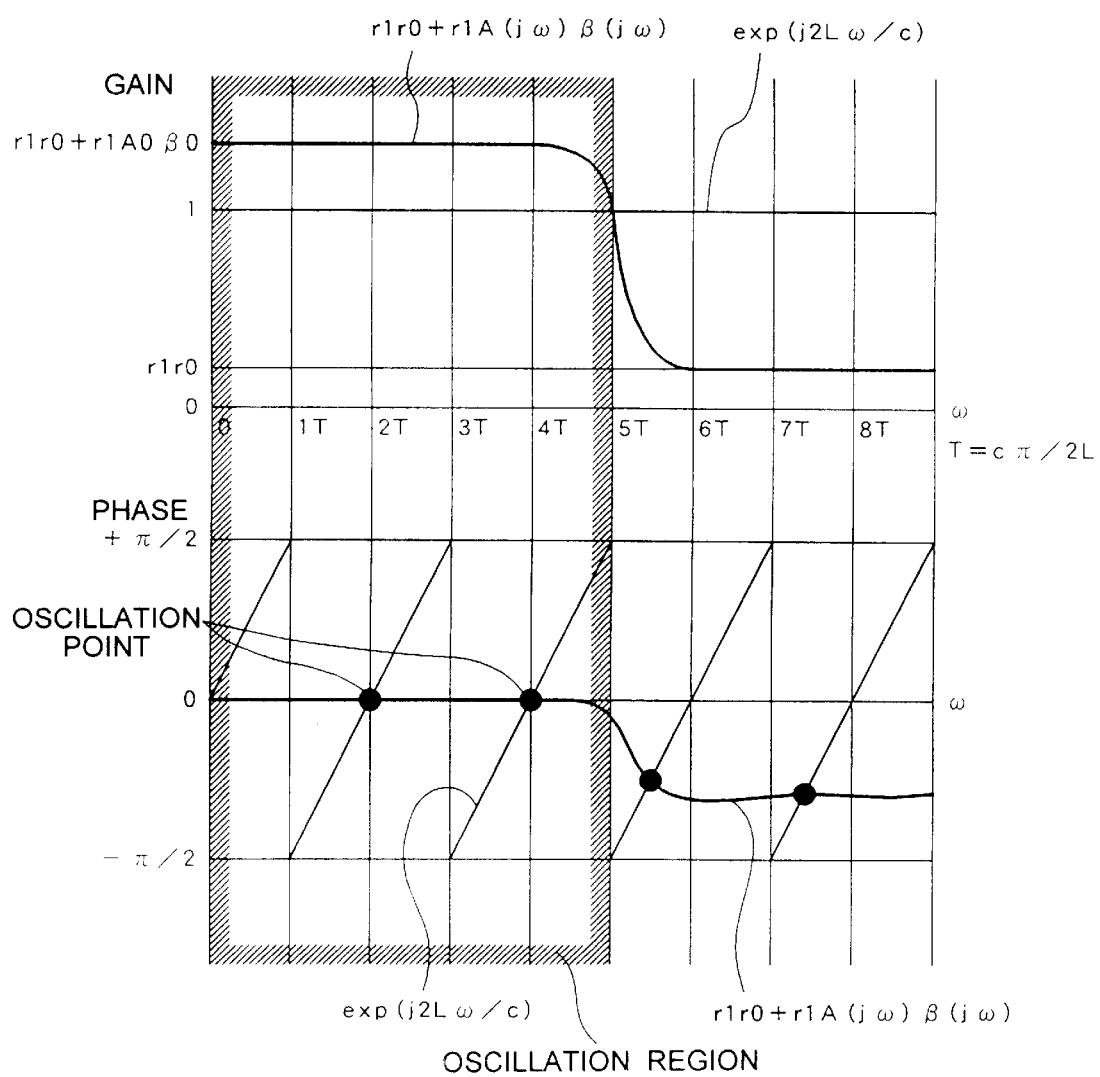
FIG. 5 is a view showing a board diagram of the positive feedback system using a low pass filter in the nondestructive testing apparatus according to Embodiment 1 of this invention.
Figure 6:
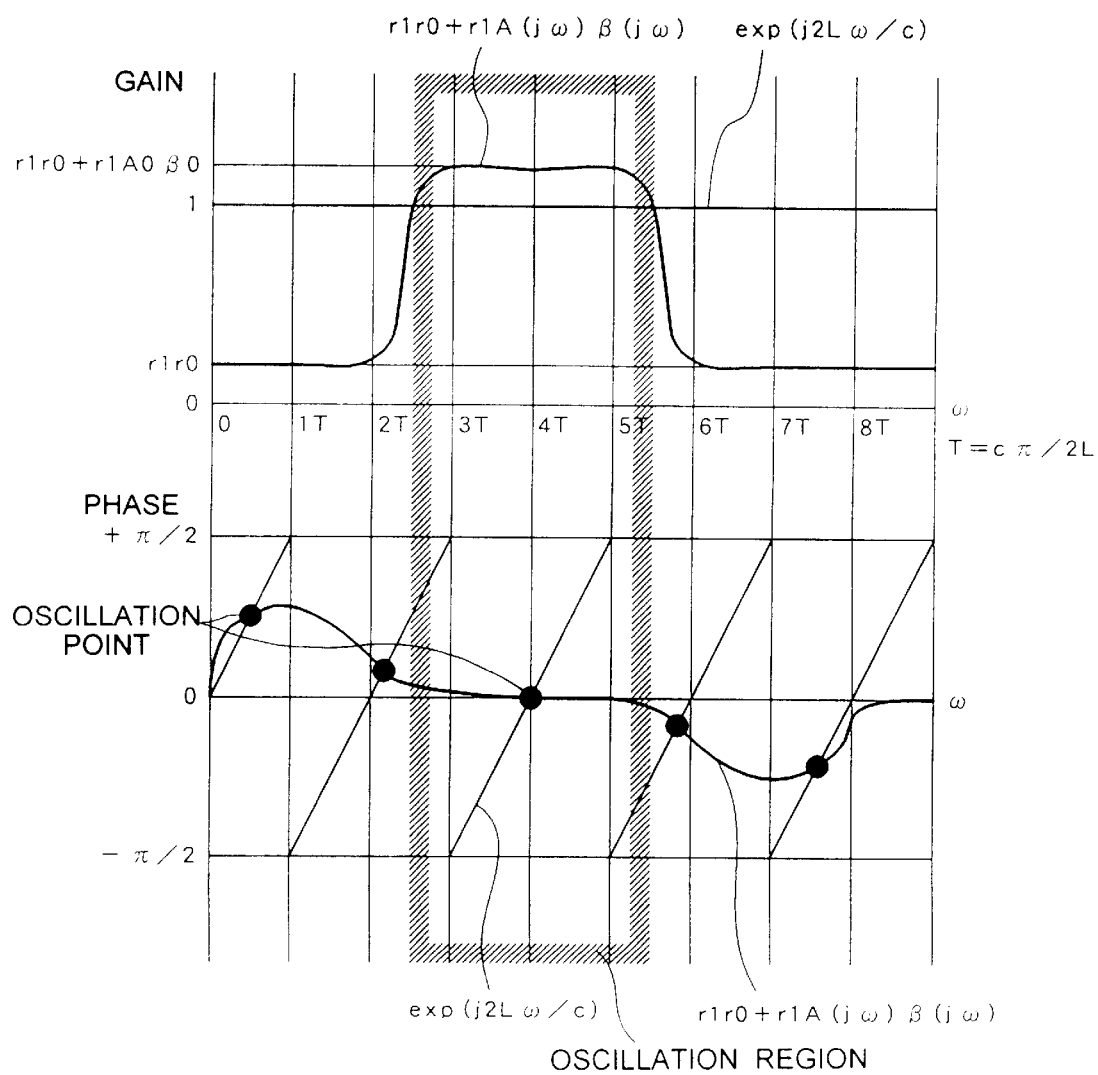
FIG. 6 is a view showing a board diagram of the positive feedback system using a band pass filter in the nondestructive testing apparatus according to Embodiment 1 of this invention.

In this case, $r_1 r_0 + r_1 A(j\omega)\beta(j\omega)$ represents the frequency dependency shown in FIGS. 5 and 6.

On the other hand, in the same manner, $e^{j\omega 2L/c}$ has the frequency dependency that the phase changes periodically at a cycle $c\pi/2L$ at the gain 1 shown in FIGS. 5 and 6.

The oscillation frequencies are in the oscillation region that meets the gain condition in FIGS. 5 and 6 showing board diagrams and are oscillation points (solid black points in the drawings) that satisfy the phase condition. In the case where the band of FIG. 5 is wide and a plurality of harmonics are included in this band, the oscillation occurs at the frequency that has the lowest order in this band.

Due to the phase characteristics of the filter, the oscillation frequency is offset from the basic frequency and its harmonic. However, the phase characteristics of the pass band are set in the vicinity of zero to thereby make it possible to keep the precision that is needed for the measurement.

Once the oscillation occurs, the oscillation frequency is stabilized. This is because, even if the frequency offset is generated by the positive feedback in which the propagation cycle is used as the basic signal, a compensation signal output for correcting it is outputted from the positive feedback, and the frequency is again converged to the oscillation frequency that is determined by the propagation cycle. Namely, when the oscillation condition is offset, the level of the reflection wave signal is lowered and the gain of the automatically amplifying rate controlling function-equipped amplifier 9 is increased.

Also, since the phase of $A\beta$ is also shifted in a direction returning to the oscillation frequency as the gain changes, the control is effected to meet the oscillation condition again.

The process to the oscillation is as follows:

(1) First of all, a trigger signal X is generated. The trigger signal may have a pulse inputted purposely therein to or may be an impact signal that is generated when the wave transmitter 20 is brought into contact with the measurement object 6.

(2) When the trigger signal is generated, the signal is amplified through the amplifier 9, and the longitudinal elastic wave is propagated to the measurement object 6 and propagated to the end face 6b and reflected thereat. Upon the reflection, an attenuation of the signal level defined by the reflection coefficient ($r_1$) is generated.

(3) The reflection wave is propagated in the opposite direction from the end face 6b toward the transmitted wave surface and is detected at the received wave surface by the wave receiver 7.

(4) The wave receiver 7 outputs this reflection wave signal to the filter 8.

(5) The filter 8 outputs the signal that is limited to the band to the automatically amplifying rate controlling function-equipped amplifier 9.

(6) The automatically amplifying rate controlling function-equipped amplifier 9 compares the signal level with the setup value. In the case where the signal level is smaller, the gain is increased on the basis of the difference therebetween. This amplified signal is outputted to the magnetically excited current feeding device 5.

(7) Out of the signal components thus far described, the frequency component that meets the oscillation condition is repeatedly circulated through the positive feedback loop, and is finally converged into a sine wave having the oscillation frequency. The change to the sine curve is due to the fact that the high frequency component or the low frequency component is attenuated by the filter within the positive feedback.

(8) The oscillation frequency $f_n$ is automatically extracted through the above-described (1) to (7).

Figure 7:
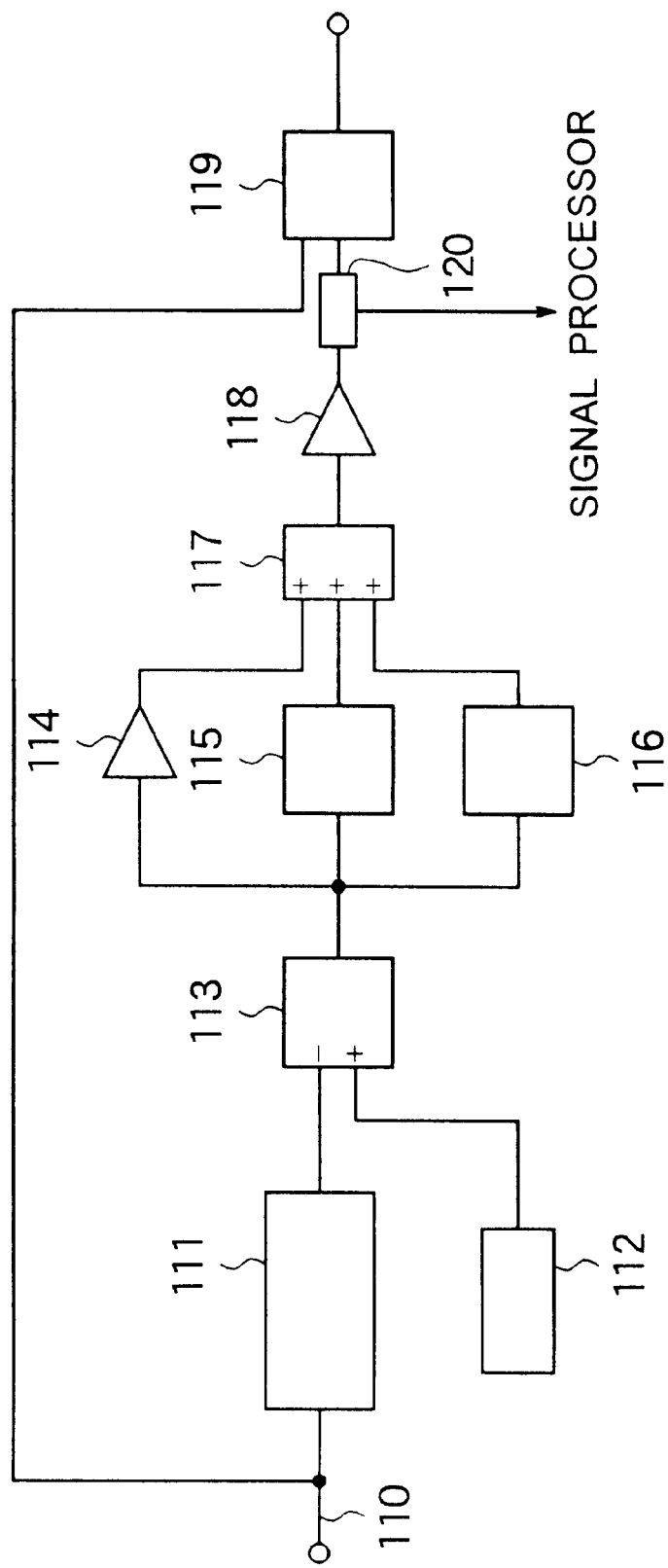
FIG. 7 is a view showing the constitution of an automatically amplifying rate controlling function-equipped amplifier in the nondestructive testing apparatus according to Embodiment 1 of this invention.

FIG. 7 is a view showing the constitution of an automatically amplifying rate controlling function-equipped amplifier. In the same drawing, reference numeral 111 denotes an RMS calculator, and reference numeral 112 denotes a level setter for setting the level of the feedback signal. Also, reference numeral 113 denotes an adder with polarities for calculating the difference of the outputs between the RMS calculator 111 and the level setter 112 and for outputting the signal to a proportional amplifier 114, an integrator 115 and a differentiator 116 thereafter. Furthermore, reference numeral 117 denotes an adder with polarities and reference numeral 118 denotes a proportional amplifier.

The above adder 113 with polarities, proportional amplifier 114, integrator 115, differentiator 116, adder 117 with polarities and proportional amplifier 118 constitute the PID calculator, to output the correction output so that the output of the RMS calculator 111 corresponds to the level set by the level setter 112. The final stage amplifier 119 amplifies the signal 110 inputted by the amplifier 120 that uses the correction output thus calculated as the gain adjustment signal and automatically controls the amplifying rate of the signal.

The RMS calculator 111 performs the square root calculation of the mean square value of the input signal and calculates the level of the input signal.

The respective gain, integration time and differentiation time of the proportional amplifiers 114 and 118, the integrator 115 and the differentiator 116 are adjusted to optimum values by a tuning method of the PID control that is generally well known.

The feature of this method is that only the wave of the frequency that matches the phase of the reflection wave is automatically selected, and kept on oscillating continuously at a single frequency by the positive feedback regardless of the level and the form of the signal of the reflection wave. This is stable and high in precision in comparison with a method of measuring the propagation time from a temporary received wave signal that attenuates, which is adopted in a conventional method.

According to the conventional method, the propagation time had to be calculated from the interval by causing the trigger waveform to correspond to the rising point or falling point of the signal of the reflection wave or the like. However, the attenuation generated within a measurement object in the propagation or the deformation of the waveform due to the diffusion occurs. It is not easy to judge this correspondence. Also, the offset of the corresponding points leads to the degradation in precision of measurement. On the other hand, according to this invention, since the phase controlling function of the positive feedback is utilized to automatically realize the oscillation of the single frequency regardless of the form of the received wave signal. Accordingly, this oscillation frequency may readily be measured with high precision by applying a Fourier function transform (FFT) feature or a frequency counting feature or the like.

Figure 8:
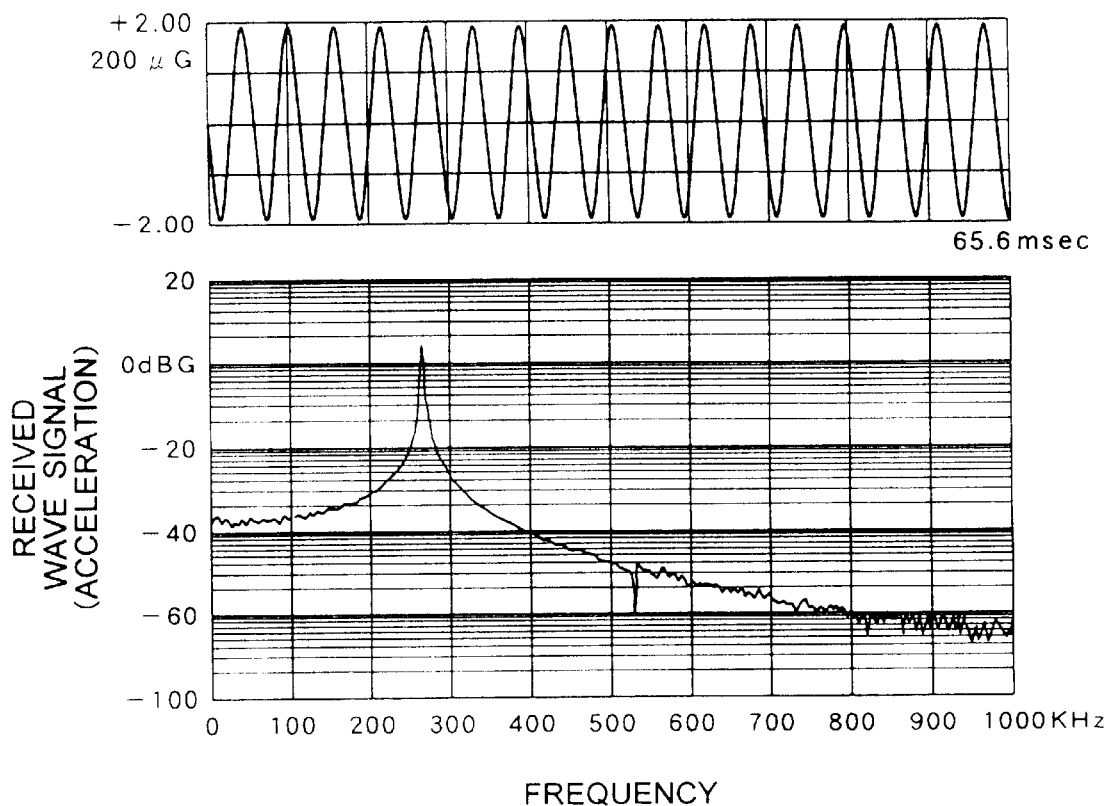
FIG. 8 is a view showing an example of an output in a frequency band in accordance with the nondestructive testing apparatus according to Embodiment 1 of this invention.

FIG. 8 shows the frequency that normally oscillates, which is expressed by a frequency region through the FFT.

Figure 9:
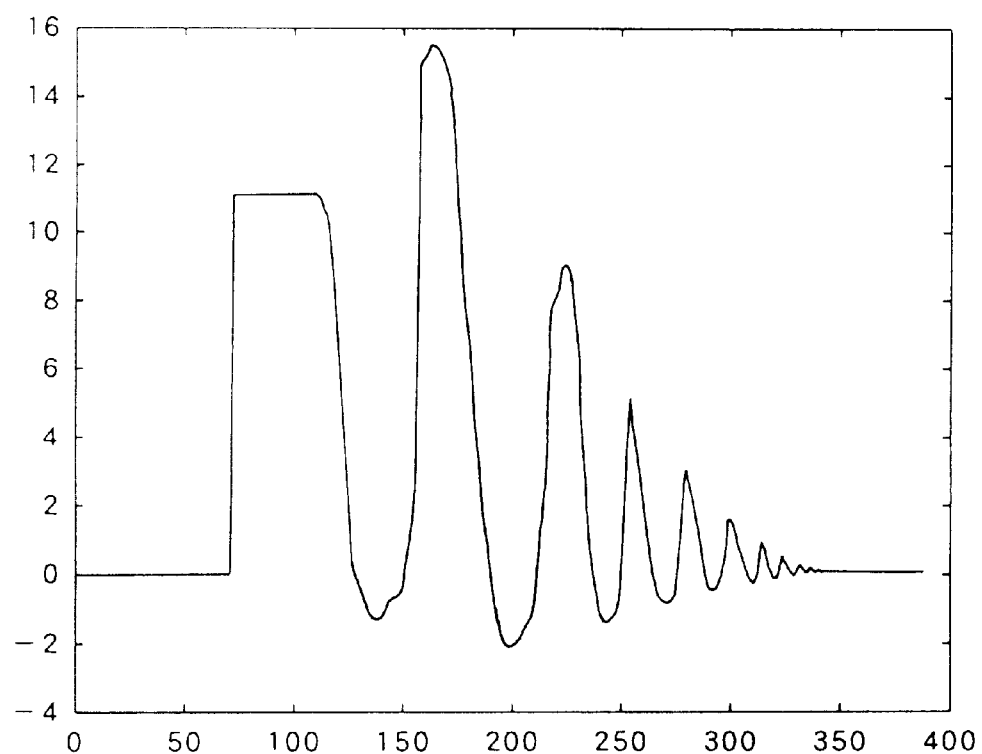
FIG. 9 is a view showing a simulation example of a control system without a positive feedback in accordance with the nondestructive testing apparatus according to Embodiment 1 of this invention.
Figure 10:
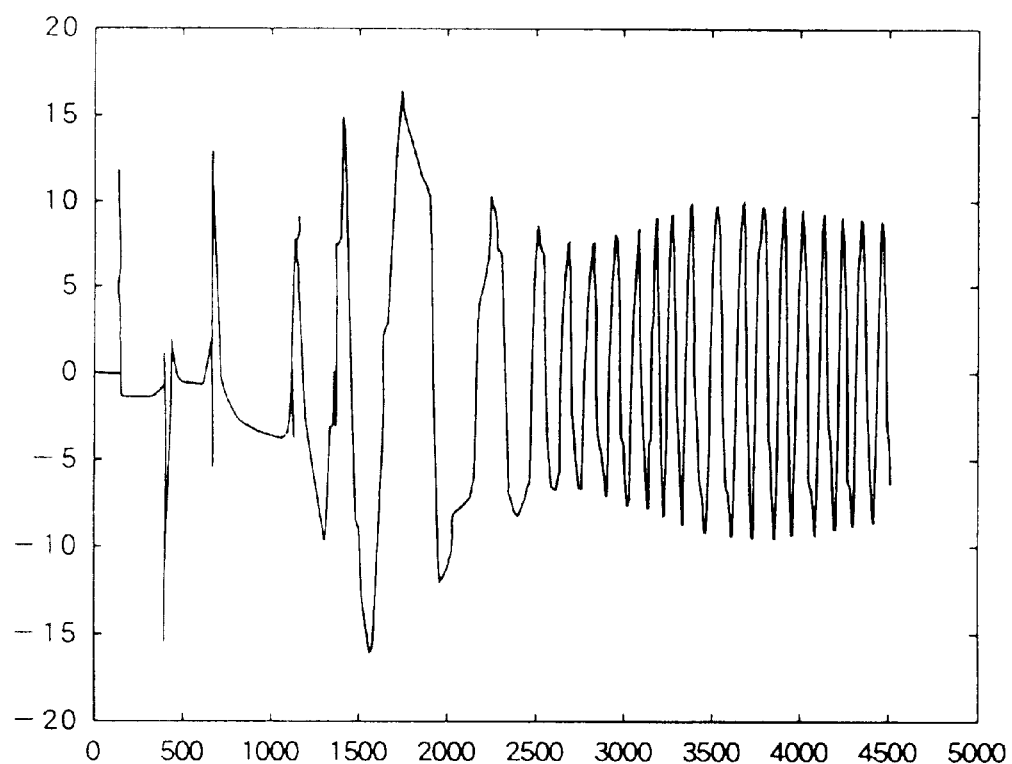
FIG. 10 is a view showing a simulation example (with the positive feedback) of the positive feedback control system of the nondestructive testing apparatus according to Embodiment 1 of this invention.

A simulation example will be shown in FIGS. 9 and 10. FIG. 9 shows the state in which the signal naturally attenuates without any action of the positive feedback. FIG. 10 shows the state in which the positive feedback works so that, after the trigger signal occurs, the signal is amplified by the feedback and the normal oscillation occurs at f=c/2L.

Figure 11:
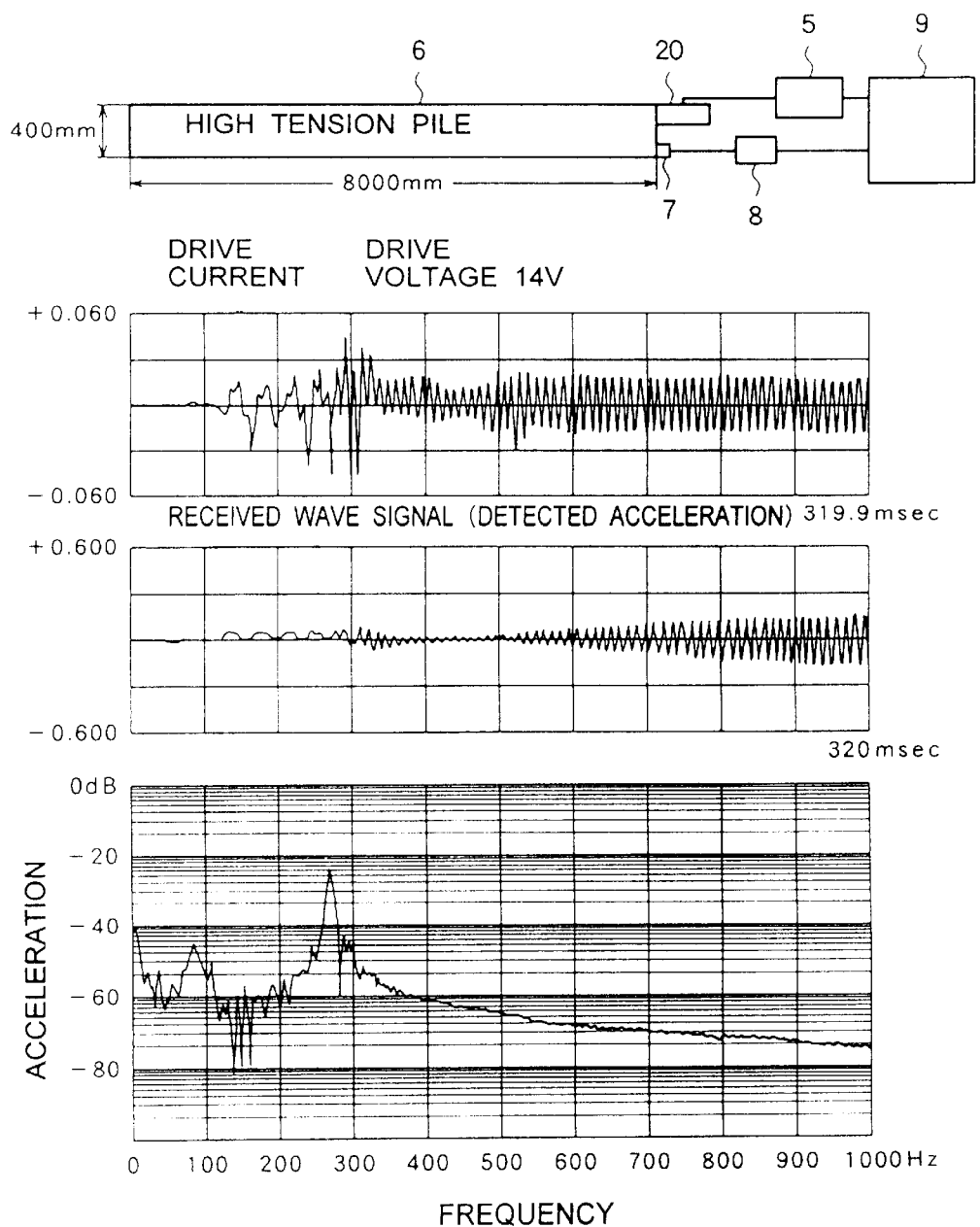
FIG. 11 is a view showing a measurement example of a transient state by the nondestructive testing apparatus according to Embodiment 1 of this invention.
Figure 12:
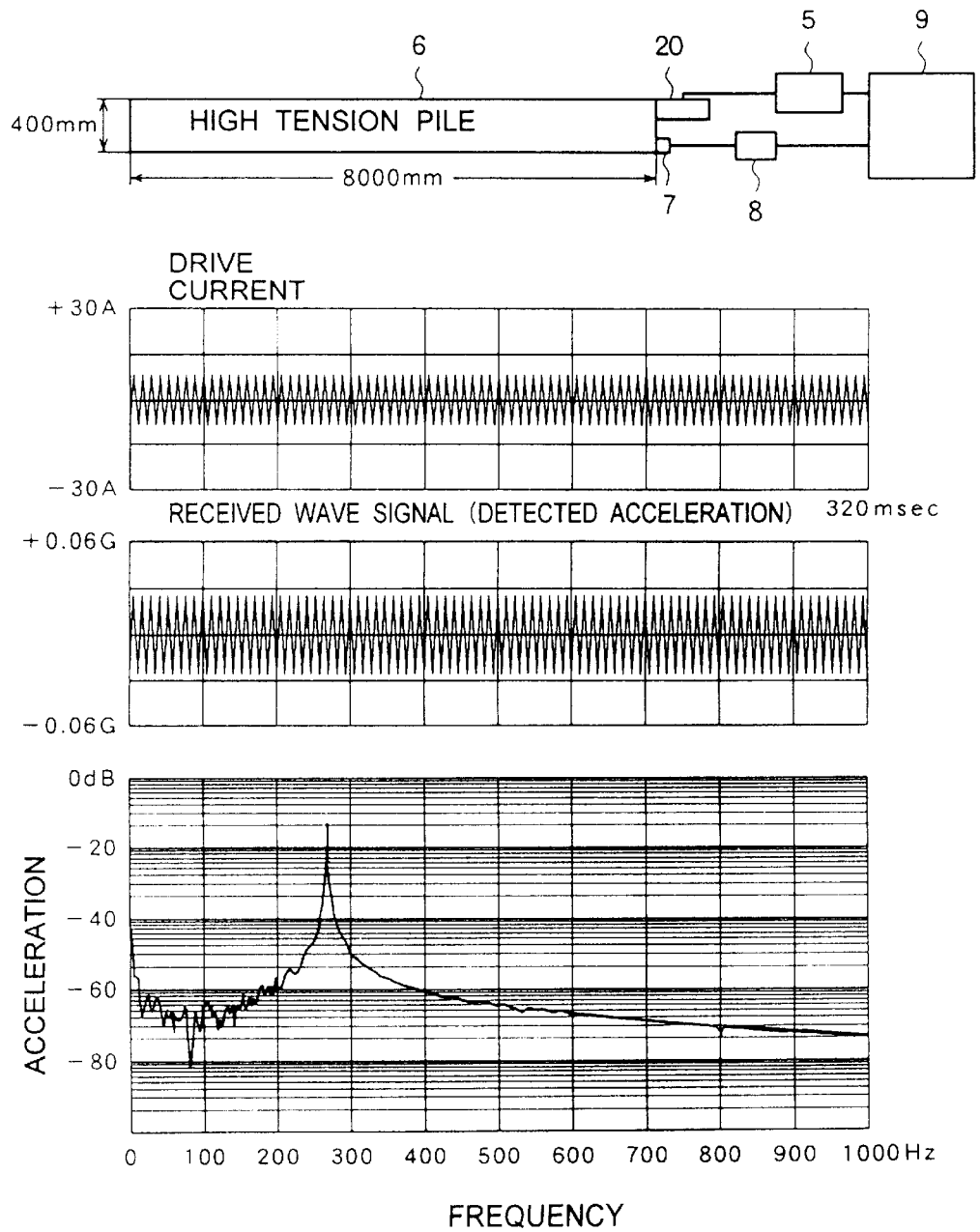
FIG. 12 is a view showing a measurement example of a normal state by the nondestructive testing apparatus according to Embodiment 1 of this invention.

Next, the measurement example is shown in FIGS. 11 and 12. FIGS. 11 and 12 show a detection example of a high tension pile at 8 m (=8,000 mm) made up of concrete structures. FIG. 11 is a view showing a transient phenomenon to the normal oscillation by the positive feedback. Also, FIG. 12 is a view showing the normal oscillation condition after the normal oscillation.

FIG. 11 shows a process in which the drive current and the received wave signal are converged to a constant frequency and a process in which the frequency spectrum thus develops a peak at the oscillation frequency.

Also, FIG. 12 shows a state in which the received wave signal may be detected in a stable manner at the oscillation frequency. This oscillation frequency is $f_1$=(4250 m/s)/(2×8 m)=266 Hz (basic frequency). Inversely, the length of 8 m may be measured from the elastic wave speed 4,250 m within the concrete pile 6.

Figure 13:
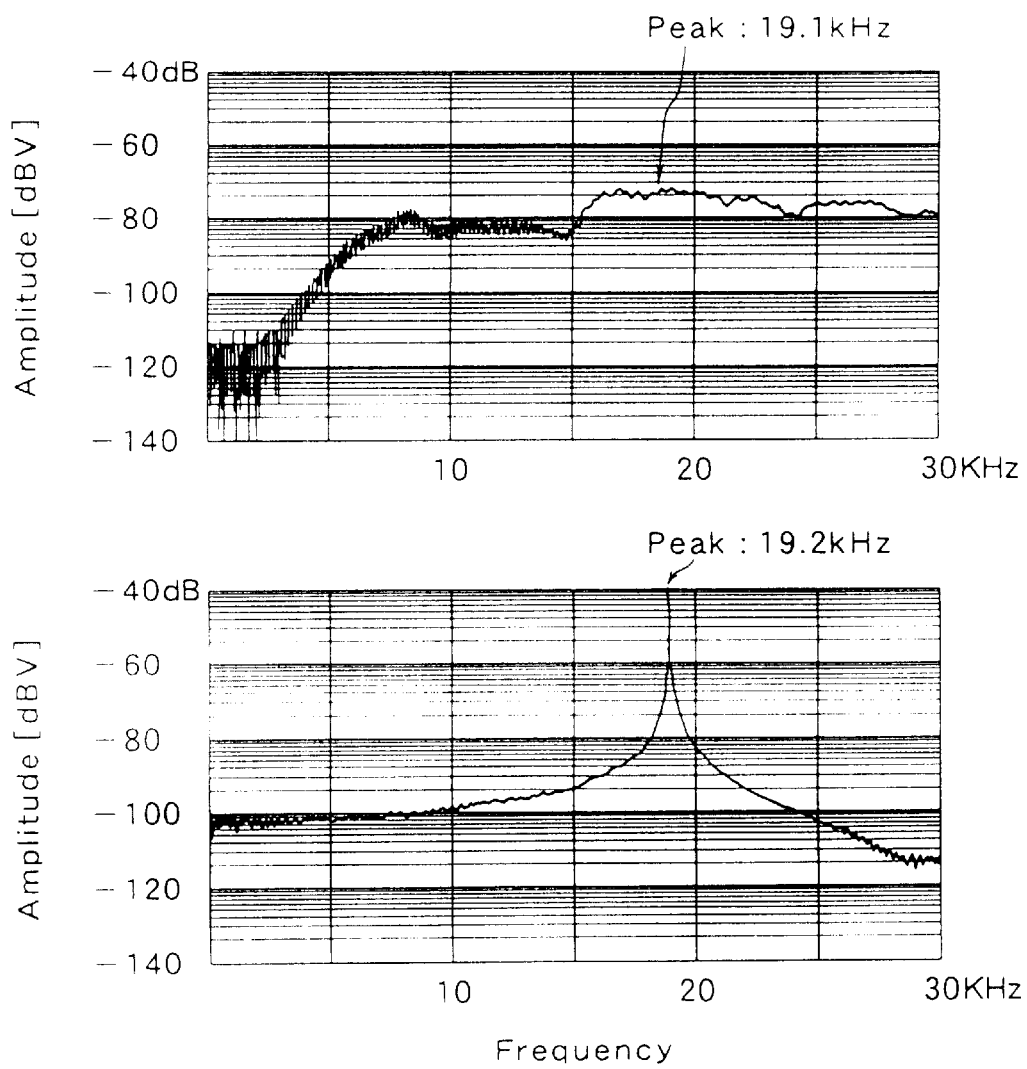
FIG. 13 is a view showing a thickness measurement example by the nondestructive testing apparatus according to Embodiment 1 of this invention.

FIG. 13 is the measurement example of the floor thickness of a concrete structure. As shown in the lowest part of the same drawing, the oscillation occurs at a frequency of f=(3,456 m/s)/(2×0.18 m)×2=19.2 kHz (secondary harmonic) corresponding to the floor thickness of 180 mm. The measurement example of the frequency sweep is also shown in the middle part of FIG. 13. It is understood that it is very difficult to determine the target frequency in the frequency sweep while the measurement using the oscillation frequency according to the present invention is easy.

As shown in the above-described measurement examples, the oscillation frequency oscillates at a frequency having a positive integer factor larger than a half-wavelength of the wavelength determined by the speed of the acoustic elastic wave. This corresponds to the distance to the reflection surface or the transmission distance. Accordingly, if the pass band of the filter 8 is set in advance in the target band out of the resonance frequency obtained by the propagation speed of the acoustic elastic wave and the transmission distance or the distance to the reflection surface, it is possible to accurately obtain the change of the sonic speed of the object 6 to be inspected, the transmission distance, the distance to the internal reflection surface, and the like.

The nondestructive testing apparatus in accordance with Embodiment 1 of this invention is provided with the wave transmitter 20 by the metal-based magnetostrictive vibrator 2, the magnetically excited current feeding device 5 for feeding the magnetically excited current to the magnetostrictive vibrator 2, the wave receiver 7 for detecting the acoustic elastic wave propagating through the measurement object 6, the automatically amplifying rate controlling function-equipped amplifier 9 for automatically controlling the amplifying rate so as to obtain a given magnitude of amplitude regardless of the magnitude of amplitude of the reflection wave or transmission wave detected by this wave receiver 7, and the filter 8 for extracting the signal of the target frequency band to be measured, which constitute the feedback loop. The apparatus is further provided with the signal processor 10 such as a calculator or the like for processing the signal detected by the above-described wave receiver 7 and the display device 11 for displaying the signal waveform detected by the above-described wave receiver 7 or the process result obtained by the above-described signal processor 10.

Namely, in the nondestructive testing apparatus according to Embodiment 1 of this invention, the magnetostrictive vibrator 2 is fixed to the concrete structure 6 to be measured, the acoustic level of the structure 6 to be measured is detected by the wave receiver 7 such as an acoustic sensor or the like, and the band limit is applied to the detected acoustic signal by the filter 8, after which the amplifying rate is automatically controlled by the automatically amplifying rate controlling function-equipped amplifier 9 so as to obtain a given signal amplitude. This is inputted into the magnetically excited current feeding device 5 of the above-described magnetostrictive vibrator 2 to form the feedback loop. For this reason, if the concrete structure 6 to be measured becomes a part of the feedback loop and the amplifying rate is suitably set, the feedback loop starts the oscillation in accordance with the pass band of the filter 8. When the pass band of the filter 8 is set appropriately, the oscillation of the resonance frequency determined by the shape of the measurement object and the propagation speed of the acoustic elastic wave occurs. This oscillation frequency is uniquely determined so that the inspection may be performed with high reproducibility and high precision.

Embodiment 2

Figure 14:
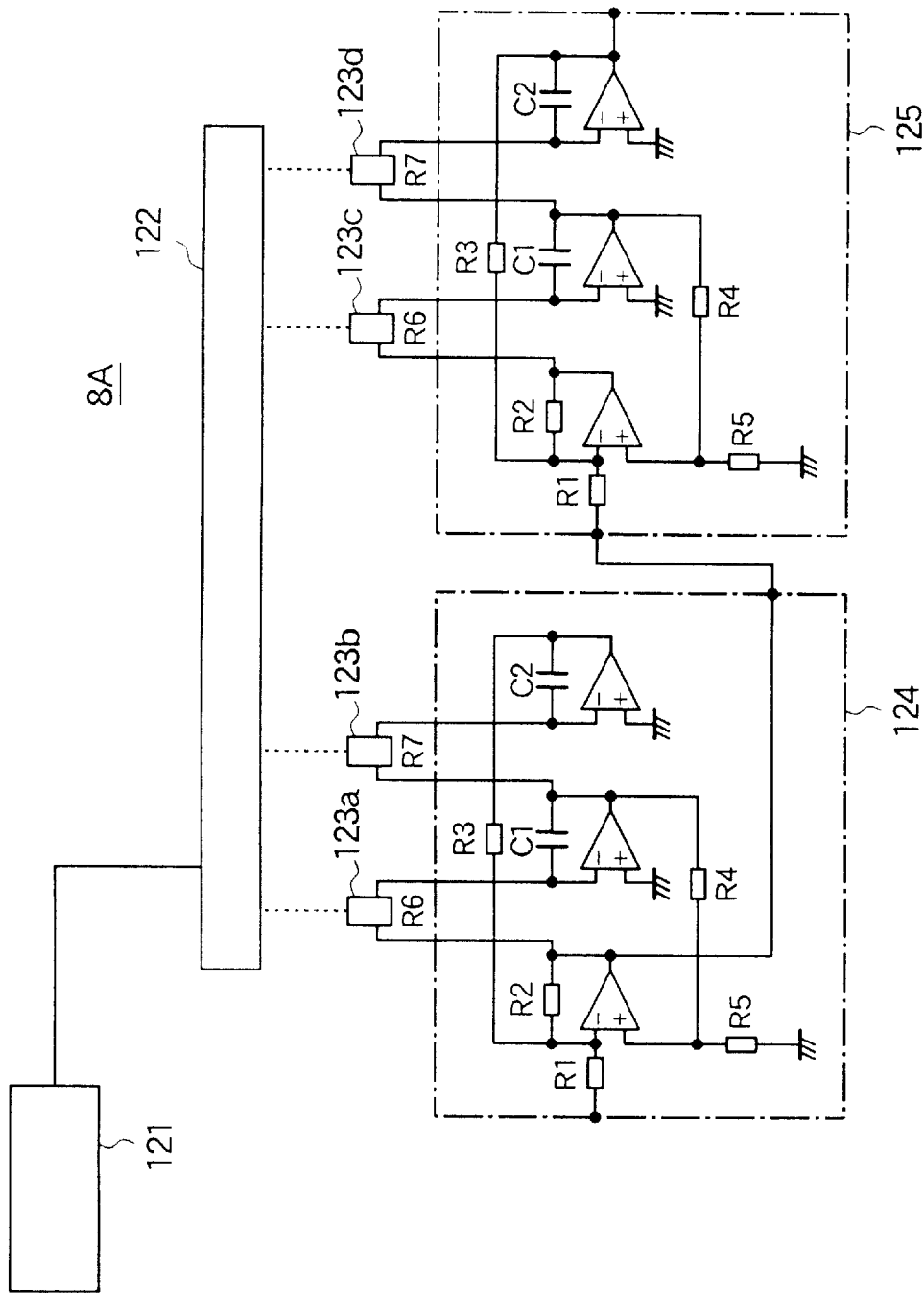
FIG. 14 is a view showing the constitution of a variable filter in accordance with a nondestructive testing apparatus according to Embodiment 2 of this invention.

A nondestructive testing apparatus according Embodiment 2 of this invention will now be described with reference to the drawings. FIG. 14 is the constitution of a variable filter of the nondestructive testing apparatus according to Embodiment 2 of this invention. In this embodiment 2, the variable filter is used instead of the filter according to Embodiment 1 but other constitution is the same as that of Embodiment 1.

FIG. 14 shows a state variable filter as an example of the variable filter 8A. In the drawing, reference numeral 121 denotes a filter characteristic setter for setting and storing a center frequency f0 and a band width B of the variable filter 8A using a keyboard (alphanumeric input keys). In the filter 8A shown in this drawing, a cascade of a high pass filter 124 and a low pass filter 125 constitutes a band pass filter. Resistors R6 and R7 within a circuit of the high pass filter 124 and resistors R6 and R7 within a circuit of the low pass filter 125 are constituted by resistor arrays 123*a*, 123*b*, 123*c* and 123*d*, respectively. Namely, in each of R6 and R7, a plurality of resistors (resistor array) are connected in parallel as desired. A resistor value controlling circuit 122 performs the calculation so as to obtain the center frequency and the band width set by the filter characteristic setter 121 in advance and controls a combination of the respective resistor arrays of R6 and R7 of the high pass filter 124 and the low pass filter 125.

Figure 15:
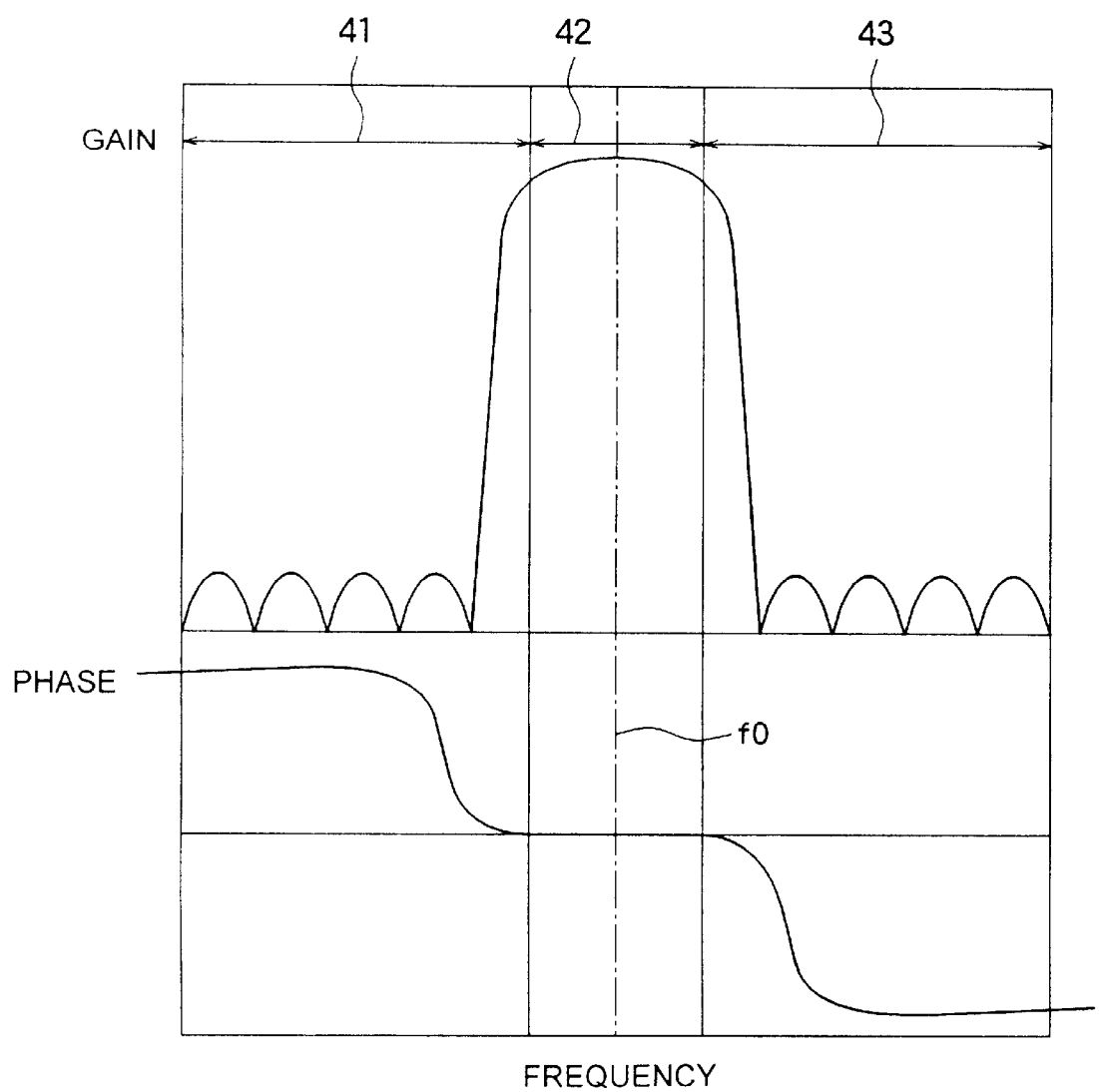
FIG. 15 is a view showing a frequency characteristic of an ideal band filter in accordance with Embodiment 2 of this invention.

FIG. 15 is a view showing a characteristic when the above-described variable filter 8A is used as an ideal band pass filter. In the drawing, reference numeral 41 represents a stop band, reference numeral 42 represents a pass band and reference numeral 43 represents a stop band. The filter having the center frequency and the band width adjustable automatically or manually, and having a narrow band is employed. The filter having a characteristic of extremely small phase change within the band width must be chosen. As an example of the filter in which the phase change is small, a Butter worth filter may be used and it is possible to design the filter with a minimum phase change at the center frequency.

Figure 16:
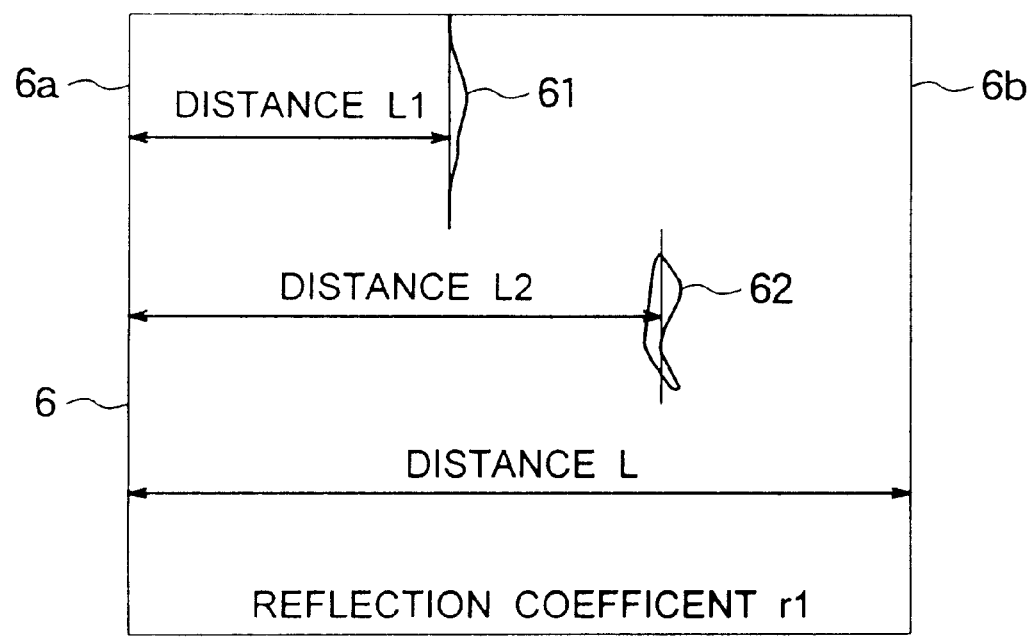
FIG. 16 is a view showing an internal structure of the measurement object in accordance with Embodiment 2 of this invention.

On the other hand, FIG. 16 is a view showing an internal structure of the measurement object 6. In the drawing, reference numeral 61 is a crack that is present in the interior, reference numeral 62 denotes an internal gap, and symbol 6*b* denotes an end face of the measurement object 6. There are various constitutions corresponding to the internal structure other than the above. However, the present embodiment will now be described while being limited to the above-described state.

Assuming that the center frequency of the filter is $f_0$ and the band width is B, the band of the filter is limited by B and ① of the oscillation condition described in conjunction with Embodiment 1 is available for only a part within the band, and the frequency capable of oscillating is selected from the phase condition ②.

More specifically, in accordance with this band, the following range is a possible measurement range.

$$L_1 = \frac{c}{2\left(f_0 + \frac{B}{2}\right)} t0 L_n = \frac{c}{2\left(f_0 - \frac{B}{2}\right)} \quad (5)$$

In other words, the value of the center frequency $f_0$ is shifted automatically or manually, so that a possible measurement range is changed and the specific range may be selectively measured.

By simultaneously satisfying the oscillation conditions ① and ②, the oscillation frequency is determined. In the case where the band of ① is wide and a plurality of oscillation frequencies are included in this band, one having a high level is selected out of the reflection waves.

With respect to Aβ, the frequency characteristic (gain, phase) is changed according to the automatically amplifying rate controlling function-equipped amplifier 9 and the filter characteristic. However, in general, a band pass filter (BPF) obtained by composing a low pass filter (LPF) and a high pass filter (HPF) is used.

In FIG. 16, the elastic wave traveling through the measurement object 6 reaches the crack 61 and the reflection wave is generated at the crack surface. When this reflection wave reaches the oscillation surface 6*a*, the propagation time corresponding to the distance may be detected. Furthermore, when another gap 62 is present behind that, the elastic wave traveling through the measurement object 6 also generates the reflection wave therein and this reflection wave also reaches the oscillation surface 6*a*.

The effect of detection of the internal structure of the measurement object 6 by the variable filter 8A in accordance with Embodiment 2 will now be described.

Figure 17:
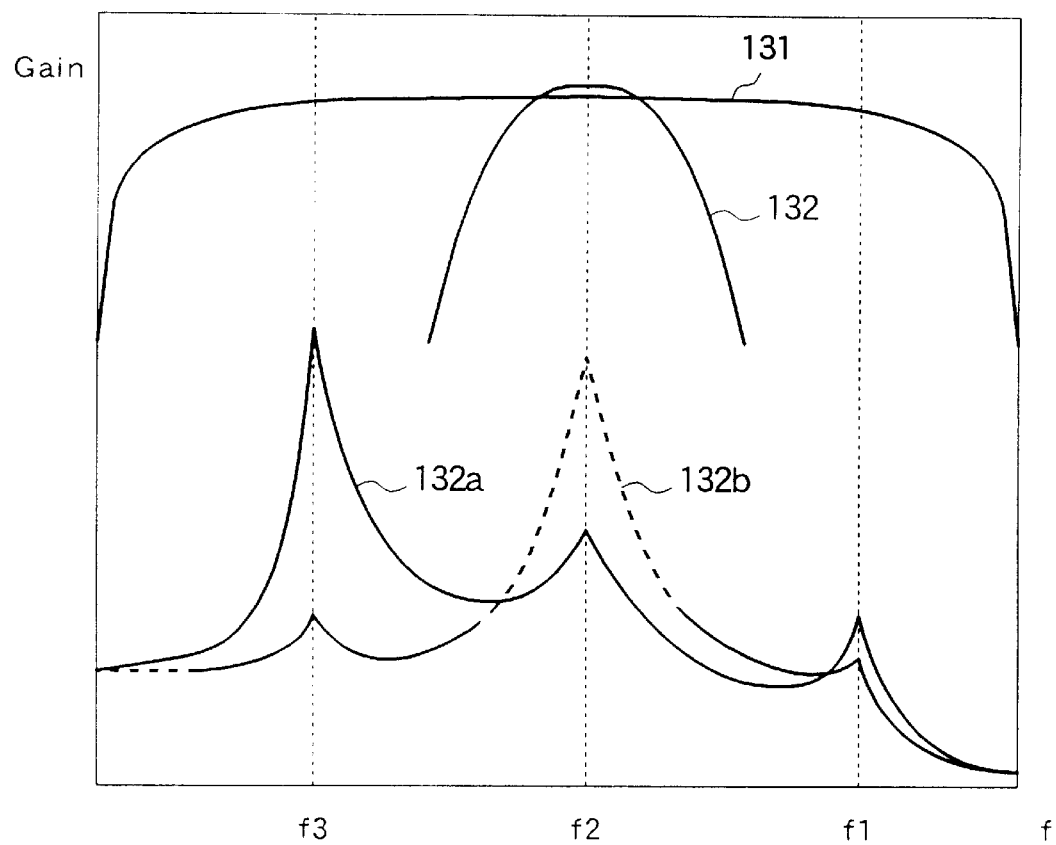
FIG. 17 is a view showing a characteristic of the variable filter of the nondestructive testing apparatus in accordance with Embodiment 2 of this invention.

FIG. 17 is a view showing the characteristic of the variable filter. In the same drawing, reference numerals 131 and 132 represent the filter characteristics in the cases where the characteristics of the variable filters have the wide band and the narrow band, respectively.

In the internal structure of the measurement object 6 shown in FIG. 16, assume that f1, f2 and f3 are the oscillation frequencies corresponding to the distance L1 to the crack 61, the distance L2 to the gap 62 and the distance L3 to the end face 6*b*, respectively.

The band width is set small in the filter character setter 121 shown in FIG. 14 so that the variable filter 8A is set to the narrow band filter 132. Also, when the designated value of the center frequency f0 is gradually increased by the resistor value controlling circuit 122 and the value is shifted from the low frequency toward the high frequency side, as shown in the initial oscillation patterns 132*a* to 132*b* of FIG. 17, the oscillation frequency is shifted. Symbol 132*b* denotes the case where the pass band of the narrow band filter 132 includes the oscillation frequency f2 in the gap 62. At this time, the oscillation frequency f2 is maximum. Thus, the void position of the internal structure of the measurement object 6 may be calculated from f2.

Thereafter, the oscillation by the positive feedback and the calculation of the oscillation frequency are the same as those in Embodiment 1. The thus far measurement process is shown by flowcharts in FIGS. 18 and 19.

Figure 18:
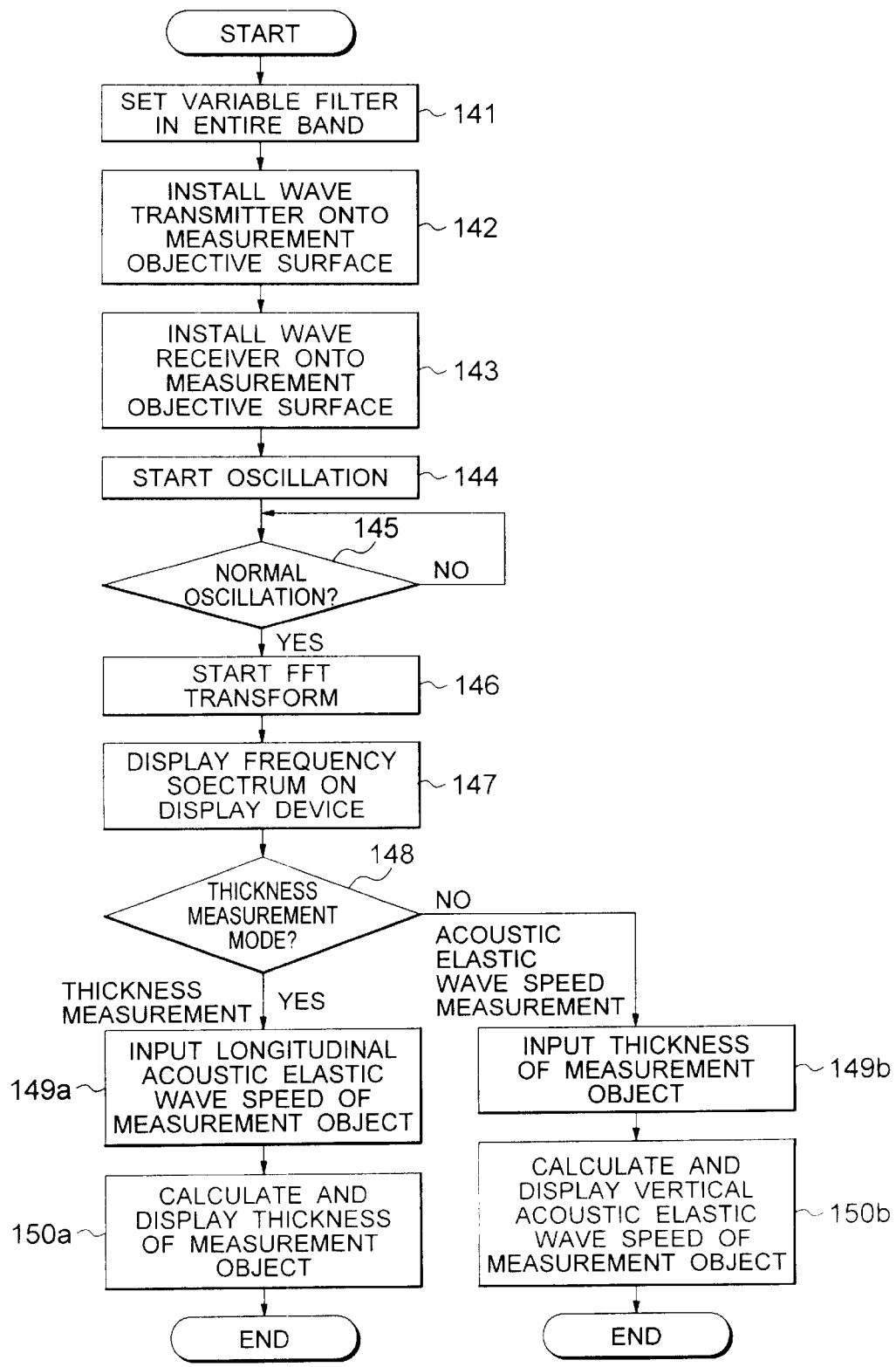
FIG. 18 is a flowchart showing an example of a measurement process using the nondestructive testing apparatus in accordance with Embodiment 2 of this invention.

Namely, in steps 141 to 144 of FIG. 18, the variable filter 8A is set in the entire band and the wave transmitter 20 and the wave receiver 7 are set on the measurement object 6. Then, the oscillation is started.

Next, in steps 145 to 147, if the constant oscillation occurs, the FFT transform is started in the signal processor 10 and the frequency spectrum is shown on the display device 11.

Next, in steps 148 to 150a, in case of a thickness measurement mode, the longitudinal acoustic elastic wave speed of the measurement object 6 is inputted, on the basis of which the thickness of the measurement object 6 is calculated by the signal processor 10. The result is shown on the display device 11.

Also, in steps 149b to 150b, in case of an acoustic elastic wave speed measurement mode, the thickness of the measurement object 6 is inputted, on the basis of which the longitudinal acoustic elastic wave speed of the measurement object 6 is calculated in the signal processor 10. The result is shown on the display device 11.

Figure 19:
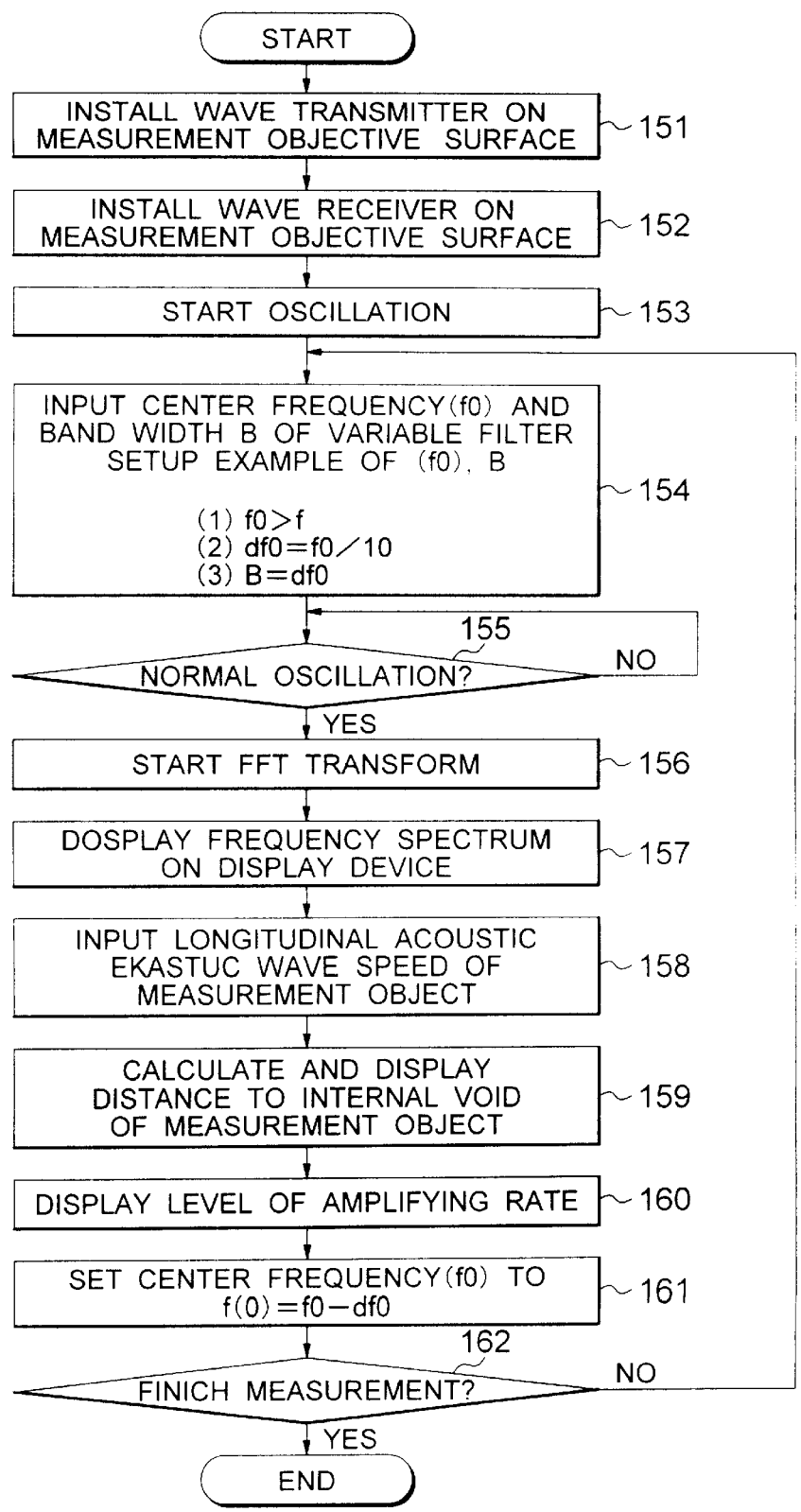
FIG. 19 is a flowchart showing another example of a measurement process using the nondestructive testing apparatus in accordance with Embodiment 2 of this invention.
Figure 20:
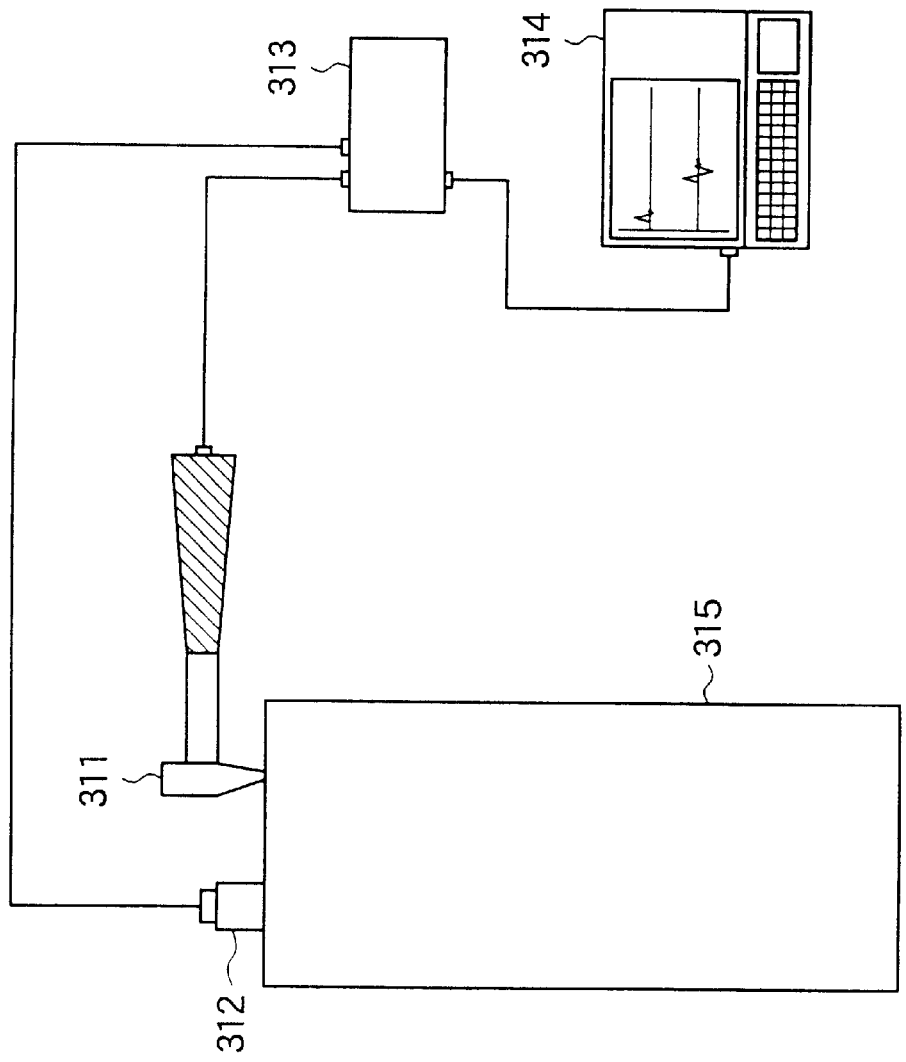
FIG. 20 is a view showing a system configuration a conventional acoustic elastic wave method by a hammer.

Also, in steps 151 to 153 of FIG. 19, the wave transmitter 20 and the wave receiver 7 are installed on the measurement object 6 and the oscillation is started.

Next, in step 154, the center frequency f0 of the variable filter 8A and the band width B are set and inputted.

Next, in steps 155 to 157, if the constant oscillation occurs, the FFT transform is started in the signal processor 10 and the frequency spectrum is shown on the display device 11.

Next, in steps 158 to 160, the acoustic elastic wave speed of the measurement object 6 is inputted, on the basis of which the thickness of the measurement object 6 is calculated in the signal processor 10. The result is shown on the display device 11. Also, this is the case in the amplifying rate of the amplitude amplifier 9 with the automatically amplifying rate controlling function.

Subsequently, in steps 161 to 162, the center frequency f0 is set to f0=f0−df0 (for example, df0=f0 /10). Then, unless the measurement is finished, the program returns to step 154, and the process from step 154 to step 161 is repeated.

The nondestructive testing apparatus in accordance with Embodiment 2 of this invention is provided with the variable filter 8A having the function to automatically or manually change the target frequency band to be measured.

Namely, in the nondestructive testing apparatus in accordance with this Embodiment 2, since the variable filter 8A in which any desired pass band may be automatically or manually set is provided in the feedback loop, any desired resonance frequency may be extracted out of the resonance frequencies of the measurement object 6. It is possible to perform the accurate inspection even if the measurement object 6 or the target frequency band to be measured is changed.

Embodiment 3

The automatically amplifying rate controlling function-equipped amplifier 9 controls the output in correspondence with the intensity level of the reflection wave signal to be detected by the positive feedback. Namely, when the reflection wave signal is small, the amplifying rate is increased, and when the reflection wave level is large, the output level is decreased.

On the other hand, the amount of reflection of the reflection wave from the measurement object 6 is changed in accordance with the crack 61 within the object or the size of the gap 62. In general, the larger the damage, the more the reflection becomes. The smaller the damage, the less the reflection becomes. For this reason, the level of the reflection wave can reflect the internal state of the measurement object 6. Namely, if the magnitude of the reflection wave signal from the measurement object 6 is detected, it is possible to know the internal state.

The following formula (6) represents the output of the automatically amplifying rate controlling function-equipped amplifier 9 in the oscillation state.

$$A\beta = \frac{1 - r_2 r_0}{r_2} = \frac{1}{r_2} - r_0 \tag{6}$$

Thus, it is understood that, the smaller the reflectivity r2, the larger the gain A of the automatically amplifying rate controlling function-equipped amplifier 9 becomes and the larger its output becomes. Thus, it is possible to infer the degree of the damage of the internal structure of the measurement object 6.

Namely, as shown in FIG. 7, the automatically amplifying rate controlling function-equipped amplifier 9 has circuits 111 to 118 for outputting the correction amount of the amplifying rate (amplifying signal 120 (gain adjustment signal)) and the signal processor 10 obtains the state information of the internal structure of the measurement object 6 in accordance with the above-described correction amount. Also, the above-described information is displayed on the display device 11.

The nondestructive testing apparatus in accordance with Embodiment 3 of this invention is provided with the automatically amplifying rate controlling function-equipped amplifier 9 having a function of measuring the magnitude of the reflection wave or the transmission wave in accordance with the control signal (correction amount) of the amplifying rate which is automatically set.

Namely, in the automatically amplifying rate controlling function-equipped amplifier 9 of the nondestructive testing apparatus in accordance with this Embodiment 3, the vibration level of the reflection wave or the transmission wave is automatically measured in accordance with the control signal of the amplifying rate. For this reason, it is possible to quantitatively detect the state of the internal structure or the abnormal portion of the measurement object 6.

INDUSTRIAL APPLICABILITY

As described above, the nondestructive testing apparatus in accordance with this invention is provided with a wave transmitter for injecting an acoustic elastic wave into a measurement object on the basis of the magnetically excited current, a magnetically excited current feeding device for feeding the magnetically excited current to the above-described wave transmitter, a wave receiver for detecting the acoustic elastic wave for propagating through the measurement object and for outputting a received wave signal, a filter for putting a band limit to the above-described received wave signal, an automatically amplifying rate controlling function-equipped amplifier for amplifying the signal outputted from the above-described filter to a given amplitude and for outputting the signal to the above-described magnetically excited current feeding device, and a signal processor for extracting from the above-described wave receiver a signal of an oscillation frequency of a positive feedback loop composed of the above-described wave transmitter, the above-described measurement object, the above-described wave receiver, the above-described filter, the above-described amplifier and the above-described magnetically excited current feeding device and for processing the signal. Accordingly, the apparatus ensures the effect that the inspection may be performed with high precision and high reproducibility.

Also, as described above, in the nondestructive testing apparatus in accordance with this invention, the above-described wave transmitter is a magnetostrictive vibrator composed of a magnetostrictive element, a magnetically exciting coil and a magnetic biasing magnet. Accordingly, the apparatus ensures the effect that the inspection may be performed with high precision and high reproducibility.

Also, as described above, the nondestructive testing apparatus in accordance with this invention is further provide with a display device for displaying the signal waveform detected by the above-described wave receiver or the process result obtained by the above-described signal processor. Accordingly, the apparatus ensures the effect that the inspection may be performed with high precision and high reproducibility.

Also, as described above, in the nondestructive testing apparatus in accordance with this invention, the above-described filter is a variable filter for selectively extracting a single frequency out of a plurality of resonance frequencies determined by the shape and the internal structure of the measurement object. Accordingly, even if a measurement object or a target frequency band to be measured is changed, it is possible to ensure the accurate inspection.

Furthermore, in the nondestructive testing apparatus in accordance with this invention, the above-described amplifier has a circuit for outputting the correction amount of the amplifying rate so that the above-described signal processor obtains the state information of the constitution of the measurement object in accordance with the correction amount. Accordingly, it is possible to quantitatively detect the condition of the abnormal portion or the internal structure of the measurement object.

What is claimed is:

1. A nondestructive testing apparatus comprising:

a wave transmitter for injecting an acoustic elastic wave into an measurement object on the basis of a magnetically excited current;

a magnetically excited current feeding device for feeding the magnetically excited current to said wave transmitter;

a wave receiver for detecting an acoustic elastic wave propagating through the measurement object and for outputting a received wave signal;

a filter for putting a band limit to the received wave signal;

an automatically amplifying rate controlling function-equipped amplifier for amplifying a signal outputted from said filter to a given amplitude and for outputting the signal to said magnetically excited current feeding device; and a signal processor for extracting from said wave receiver a signal of an oscillation frequency of a positive feedback loop composed of said wave transmitter, the measurement object, said wave receiver, said filter, said amplifier and said magnetically excited current feeding device and for processing the signal.

2. The nondestructive testing apparatus according to claim 1, wherein said wave transmitter is a magnetostrictive vibrator composed of a magnetostrictive element, a magnetically exciting coil and a magnetic biasing magnet.

3. The nondestructive testing apparatus according to claim 2, further comprising a display device for displaying the signal waveform detected by said wave receiver or the process result obtained by said signal processor.

4. The nondestructive testing apparatus according to claim 3, wherein said filter is a variable filter for selectively extracting a single frequency out of a plurality of resonance frequencies determined by a shape and an internal structure of the measurement object.

5. The nondestructive testing apparatus according to claim 3, wherein said amplifier has a circuit for outputting a correction amount of an amplifying rate so that said signal processor obtains state information of the constitution of the measurement object in accordance with the correction amount.

* * * * *